United States Patent [19]

Glaser et al.

[11] Patent Number: 5,466,668
[45] Date of Patent: Nov. 14, 1995

[54] SUPERIOR THROMBOMODULIN ANALOGS FOR PHARMACEUTICAL USE

[75] Inventors: Charles B. Glaser; Michael J. Morser, both of San Francisco; David R. Light, San Mateo, all of Calif.

[73] Assignee: Schering Aktiengesellschaft, Berlin, Germany

[21] Appl. No.: 155,346

[22] Filed: Nov. 22, 1993

Related U.S. Application Data

[63] Continuation of Ser. No. 568,456, Aug. 15, 1990, abandoned, which is a continuation-in-part of Ser. No. 506,325, Apr. 9, 1990, Pat. No. 5,256,770, which is a continuation-in-part of Ser. No. 406,941, Sep. 13, 1989, abandoned, which is a continuation-in-part of Ser. No. 345,374, Apr. 28, 1989, abandoned.

[51] Int. Cl.$^6$ .................................................. A61K 35/14
[52] U.S. Cl. .................................................. 514/12; 514/8
[58] Field of Search ........................................... 514/8, 12

[56] References Cited

PUBLICATIONS

Preissner et al. "Domain Structure of Endothelial . . . Anticoagulant Functions", J. Biol. Chem., vol. 265, No. 9, pp. 4915–4922 (1990).
Bourin et al., "Functional Domains of Rabbit Thrombomodulin", PNAS, vol. 83, pp. 5924–5928 (1986).
Lin et al., "Modulation of Glycosaminoglycan . . . Thrombomodulin", J. Biol. Chem., pp. 25021–25030 (1991).
Esmon, N. L., et al., "Isolation of a Membrane–bound Cofactor for Thrombin–catalyzed Activation of Protein C," J. Biol. Chem. 257:859–864 (1982).
Salem, H. H, et al., "Isolation and Characterization of Thrombomodulin from Human Placenta," J. Biol. Chem. 259:12246–12251 (1984).
Jackman, R. W., et al., "Characterization of a thrombomodulin cDNA reveals structural similarity to the low density lipoprotein receptor," PNAS 83:8834–8838 (1986).
Jackman, R. W., et al., "Human thrombomodulin gene is intron depleted: Nucleic acid sequences of the cDNA and gene predict protein structure and suggest sites of regulatory control," PNAS 84:6425–6429 (1987).

Wen, D., et al., "Human Thrombomodulin: Complete cDNA Sequence and Chromosome Localization of the Gene," Biochemistry, 26:4350–4357 (1987).
Kurosawa, S., et al., "A 10–kDa Cyanogen Bromide Fragment from the Epidermal Growth Factor Homology Domain of Rabbit Thrombomodulin Contains the Primary Thrombin Binding Site," J. Biol. Chem. 263:5993–5996 (1988).
Zushi, M., et al., "The Last Three Consecutive Epidermal Growth Factor–like Structures of Human Thromobomodulin Comprise the Minimum Functional Domain for Protein C–activating Cofactor Activity and Anticoagulant Activity," J. Biol. Chem. 264(18):10351–10353 (1989).
Bourin, M. C., et al., "Functional domains of rabbit thrombomodulin," Pro. Natl. Acad. Sci. USA 83:5924–5928 (1986).
Preissner, K. T., et al., "Domain Structure of the Endothelial Cell Receptor Thrombomodulin as Deduced from Modulation of Its Anticoagulant Functions," J. of Biol. Chem. 265–(9):4915–4922 (1990).
"Prevention of Venous Thrombosis and Pulmonary Embolism," Consensus Development Conference Statement, NIH 6(2):1–23 (Mar., 1986).
Ishii, H., et al., "Thrombomodulin Is Present in Human Plasma and Urine," J. Clin. Inv. 76:2178–2181 (1985).
Stearns, D. J., et al., "Microthrombomodulin: Residues 310–486 from the Epidermal Growth Factor Precursor Homology Domain of Thrombomodulin will Accelerate Protein C Activation," J. Biol. Chem. 264:3352–3356 (1989).

Primary Examiner—Jill Warden
Assistant Examiner—P. Lynn Touzeau
Attorney, Agent, or Firm—Millen, White, Zelano, & Branigan

[57] ABSTRACT

The present invention relates to the use of analogs of thrombomodulin ("TM") that have the ability to enhance the thrombin-mediated activation of protein C but which have a significantly reduced ability to inhibit the direct procoagulant activities of thrombin, such as, for example, thrombin-mediated conversion of fibrinogen to fibrin. These analogs are useful in, for example, antithrombotic therapy. Novel proteins, nucleic acid gene sequences, pharmaceuticals and methods of inhibiting thrombotic activity are disclosed. Included are methods for increasing the circulating half life of the proteins.

26 Claims, 3 Drawing Sheets

SUPERIOR THROMBOMODULIN ANALOGS FOR PHARMACEUTICAL USE

This application is a continuation of application Ser. No. 07/568,456, filed Aug. 15, 1990, now abandoned, which is a continuation-in-part of Ser. No. 07/506,325 filed Apr. 9, 1990, now U.S. Pat. No. 5,256,770, which is a continuation-in-part of Ser. No.07/406,941 filed Sep. 13, 1989, now abandoned, which is a continuation-in-part of Ser. No. 07/345,374 filed Apr. 28, 1989, now abandoned.

BACKGROUND OF THE INVENTION

1. Field of the Invention

The present invention relates to the use of analogs of thrombomodulin ("TM") that have the ability to enhance the thrombin-mediated activation of protein C but which have a significantly reduced ability to inhibit the direct procoagulant activities of thrombin, such as, for example, thrombin-mediated conversion of fibrinogen to fibrin. These analogs are useful in, for example, antithrombotic therapy. Novel proteins, nucleic acid gene sequences, pharmaceuticals and methods of inhibiting thrombotic activity are disclosed. Included are methods for increasing the circulating half life of the proteins.

There are many disease states that would benefit from treatment with a safe and effective anticoagulant/antithrombotic. The nature of these conditions varies. For example, anticoagulant therapy is useful in acute conditions such as during thrombolytic therapy in myocardial infarction or in treatment of disseminated intravascular coagulation (DIC) associated with, for example, septicemia. Anticoagulants are also useful for less acute conditions, such as chronic use in patients that have received heart valve implants or prophylactic use in surgery patients to reduce the risk of deep venous thrombosis (DVT).

Information Disclosure

Thrombomodulin is a membrane protein that has demonstrated anticoagulant properties. Its physiological importance has been studied. (See, for example, N Esmon, et al., (1982) *J. Biol. Chem.* 257:859–864, H. Salem, et al., (1983) *J, Biol. Chem.* 259:12246–12251).

The gene encoding native thrombomodulin has been isolated and sequenced from several species, both in its genomic form and as a cDNA (Jackman, R., et al., (1986) pNAS 83:8834–8838 and (1987) 84:6425–6429, both of which are herein incorporated by reference). Comparisons with known proteins, such as the LDL receptor, have suggested functional domains (Wen, D., et al., (1987) *Biochemistry* 26:4350–4357). One study has suggested that the fifth and sixth epidermal growth factor (EGF)-like domains have the capacity to bind thrombin (Kurosawa, S., et al., (1988) *J. Biol. Chem.* 263:5993–5996; another suggests that EGF-like domains 4, 5, and 6 are sufficient to act as a cofactor for thrombin-mediated protein C activating activity. (Zushi, et al., (1989) *J. Biol. Chem.* 264:10351–10353). Inhibition of thrombin's direct procoagulant activity (conversion of fibrinogen to fibrin) has been attributed to glycosaminoglycan substituents on the thrombomodulin molecule. (Bourin, M. C. et al., (1986) *Pro. Natl. Acad. Sci. USA* 83:5924–5928.g) The O-linked glycosylation domain has potential sites for the addition of these types of sulfated sugars.

Treatment of thrombomodulin with chondroitinase ABC, an enzyme which specifically digests certain sulfated O-linked carbohydrates such as glycosaminoglycans, renders thrombomodulin much less capable of inhibiting thrombin-mediated platelet aggregation and thrombin-mediated conversion of fibrinogen to fibrin, the primary matrix component of thrombi. (Preissner, K. T., et al., (1990) *J. of Biol. Chem.* 265-(9):4915–4922.)

Anticoagulants currently approved for use in humans are not uniformly effective and a need exists for more efficacious compounds (See, for example, Prevention of Venous Thrombosis and Pulmonary Embolism, Consensus Development Conference Statement, NIH, 1986, 6(2):1–23).

Thrombomodulin in its native form is not suitable for anticoagulant therapy as it is membrane-bound, due to its inherent amino acid sequence, and is insoluble without detergent treatment. It is present in such small amounts (about 300 mg thrombomodulin/person) that purification from autopsy or biopsy samples is impractical.

Soluble thrombomodulin-like molecules have been detected at very low amounts in human plasma and urine. These molecules have a reduced ability to promote protein C activation, and it is possible that they have been rendered at least partially inactive, due at least in part, to oxidation. It has been suggested that these molecules are degradation products of the membrane bound molecule (Ishii, H. and Majerus, P., (1985) *J. Clin. Inv.* 76:2178–2181), but they are present in such low amounts that they have been difficult to characterize (~0.8 mg/adult male). Proteolytic fragments of the purified native molecule have been produced using trypsin or elastase. (See, Ishii, supra, Kurosawa, et al., (1988) *J. Biol. Chem.* 263:5593–5996 and Stearns, et al., (1989) *J. Biol. Chem.* 264:3352–3356). Some of these fragments retain the ability to promote thrombin-mediated activation of protein C in vitro.

There is a need for new compositions that exhibit the anticoagulant properties of thrombomodulin, are soluble in plasma, are resistant to inactivation by exposure to oxidants, and are easily produced in large quantities. The present invention fulfills these and other needs.

SUMMARY OF THE INVENTION

This invention provides methods for treating thrombotic disease by administering an effective dose of a thrombomodulin analog having approximately native ability to potentiate thrombin-mediated activation of protein C and having a reduced ability to inactivate thrombin-mediated conversion of fibrinogen to fibrin. It is preferred that the analog is soluble in aqueous solution and/or oxidation resistant.

It is also preferred that the analog be modified in the sugar residues of the O-linked glycosylation domain. By modified it is meant that the O-linked glycosylation domain has an altered glycosylation pattern. This can encompass substitution, and total or partial deletion of native sugar residues. This modification can be achieved by deleting the amino acid residues that are recognized by cells as glycosylation sites. Alternatively the sugars can be chemically removed, either partially or totally. In another modification the sugars can be enzymatically treated to remove sulfate substituents. In yet another modification the entire glycosylation domain can be deleted.

It is preferred that the analogs for use in the method will retain the capacity to potentiate the thrombin-mediated activation of protein C and 80% or less of the capacity of native thrombomodulin to inactivate thrombin-mediated conversion of fibrinogen to fibrin. More specifically, the TM analogs of this invention, when standardized to have an equal activity in a standard protein C activation assay compared to native detergent-solubilized rabbit thrombomodulin, will have only 80% or less of the activity of the same amount (mass) of native thrombomodulin in a standard assay measuring thrombin-mediated conversion of fibrinogen to fibrin. A preferred analog of this invention has 50% or less of the activity of the same amount of native thrombomodulin in the fibrin assay. These capacities are measured using standard assays described herein.

This invention further provides for sterile compositions for treating thrombotic disease in mammals comprising a unit dosage of a thrombomodulin analog having the ability to potentiate the thrombin-mediated activation of protein C and a significantly reduced ability to inactivate thrombin-mediated conversion of fibrinogen to fibrin. The preferred analogs are as described above for the method.

This invention further provides for methods of increasing the in vivo circulating half life of a thrombomodulin analog comprising removing all or most of the sugar moieties in the 6 EGF-like domains.

DEFINITIONS

Figure 1:
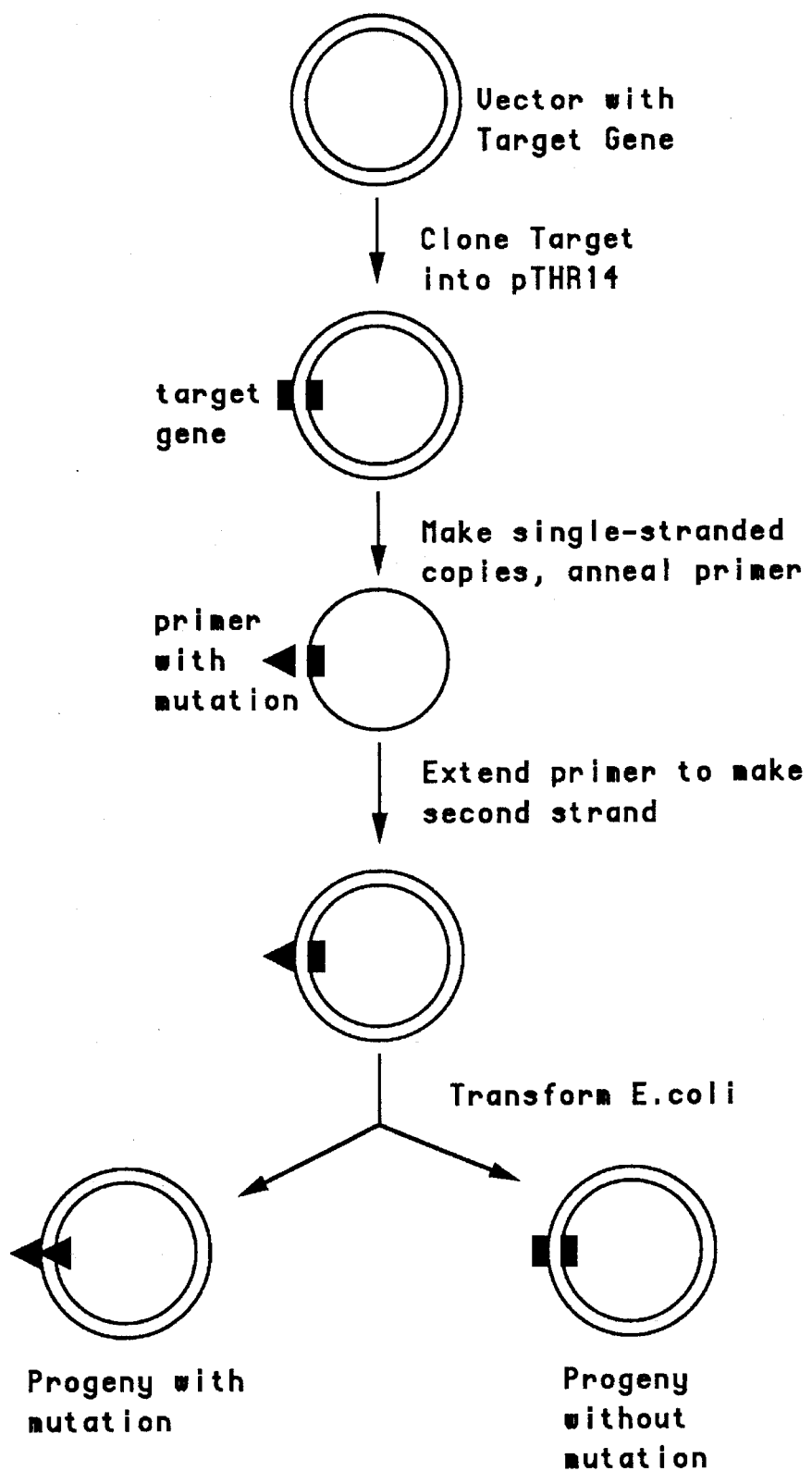
FIG. 1 is a diagram depicting the process of site-directed mutagenesis.

For purposes of the present invention the following terms are defined below.

"Glycosylation sites" refer to amino acid residues which are recognized by a eukaryotic cell as locations for the attachment of sugar residues. The amino acids where sugars are attached are typically Asn (N-linkage), threonine or serine (O-linkage) residues. The specific site of attachment is signaled by a sequence of amino acids, Asn-X-(Thr or Ser) for N-linked attachment and (Thr or Ser)-X-X-Pro for O-linked attachment, where X is any amino acid. The recognition sequence for glycosaminoglycans (a specific type of sulphated sugar) is Ser-Gly-X-Gly. The terms N-linked and O-linked refer to chemical group that serves as the attachment site between the sugar molecule and the amino acid residue. N-linked sugars are attached through an amino group; O-linked sugars are attached through an hydroxyl group.

"In vivo circulating half life" refers to the average time it takes a mammal to clear one half of the composition administered to it.

"Native thrombomodulin" refers to the full length protein as it occurs in nature. When biological activities are described with reference to the native TM, the term embraces a detergent solubilized aqueous form.

"O-linked glycosylation domain" refers to the sequence of amino acids numbered from 463 through 485 of the native thrombomodulin sequence as depicted in Table 1.

"Oxidation resistant analogs" refers to analogs of thrombomodulin which are able to maintain a substantial amount of biological activity after exposure to oxidation agents such as oxygen radicals, Chloramine T or hydrogen peroxide.

"Pharmaceutical excipients" refers to non-toxic, medically-acceptable materials which are used to complete a medical therapeutic. These materials can be inert, such as water and salt, or biologically active, such as an antibiotic or analgesic.

"Reduced ability" refers to a statistically meaningful lowering of a biological property. The property is unlimited and the measurement or quantification of the property is by standard means.

"Sugar residues" refers to hexose and pentose carbohydrates including glucosamines and other carbohydrate derivatives and moieties which are covalently linked to a protein.

"Sulfate substituents" are sulfur containing acids on pentose or hexose sugars.

"Thrombin-mediated conversion of fibrinogen to fibrin" refers to the enzymatic activity by which thrombin cleaves the precursor protein fibrinogen to make fibrin monomer which subsequently polymerizes to form a blood clot.

"Thrombotic disease" refers to a pathogenic condition in a mammal characterized by the formation of one or more thrombi that are or can be detrimental to the health of the mammal.

"Thrombomodulin analogs" refers to proteins having an amino acid sequence identical with that of native thrombomodulin, insoluble and soluble thrombomodulin peptides or fragments, and oxidation resistant TM species, all having thrombomodulin-like activity. These compounds also include derivatives and amino acid changes which do not significantly alter the protein C activation cofactor properties of the protein when compared with native TM.

"Transfer vector" refers to a vector cotransfected into an insect cell with a wild-type baculovirus. The transfer vector is constructed in such a way as to encourage a recombination between the baculovirus genome and the transfer vector, replacing the baculovirus polyhedron gene with a heterologous target gene. Where a vector is being maintained by a host cell, the vector may either be stably replicated by the cells during mitosis as an autonomous structure, or is incorporated within the host's genome.

DETAILED DESCRIPTION

In accordance with the present invention, novel methods and compositions are provided which treat thrombotic disease with an analog of thrombomodulin (TM) which retains native thrombomodulin's capacity to potentiate the thrombin-mediated activation of protein C while exhibiting a reduced capacity to inhibit the direct procoagulant activities of thrombin such as, for example, thrombin-mediated conversion of fibrinogen to fibrin. Pharmacologists prefer drugs which have a specific and limited effect upon the patient. Such drugs are preferred because they are less likely to induce undesired side effects than drugs having multiple pharmacologic effects upon a patient. This invention has the advantage of treating a single aspect of the coagulation cascade while not impacting other aspects of the cascade.

In another embodiment, this invention provides for methods of increasing the in vivo half life of TM analogs by modifying or deleting the native glycosylation patterns. Increased half-life is advantageous for TM therapy because it permits administration of lesser amounts of TM to achieve equivalent pharmacological effect compared to the native drug and a half-life which is at least greater than a few minutes provides for a more predictable therapeutic regimen.

In addition, these soluble thrombomodulin analogs can be produced economically and are easily purified and administered. A variety of therapeutic uses are anticipated, particularly with respect to anticoagulant and/or antithrombotic therapies. In order to fully appreciate the invention, the following detailed description is set forth.

I. BIOLOGICAL ACTIVITY OF THROMBOMODULIN

The underlying pathology of thrombotic disorders is that a clot forms in response to a stimulus such as, for example, a damaged vessel wall. This stimulus triggers the coagulation cascade and thus generates thrombin which has the ability to convert fibrinogen to fibrin, the matrix of the clot. Thrombomodulin is an endothelial cell membrane protein that acts as a receptor for thrombin. In humans it is distributed on the endothelium of the blood vessels and lymphatics of all organs except the central nervous system. Thrombin has the ability to bind reversibly to thrombomodulin. When bound to thrombomodulin, thrombin is converted from a procoagulant enzyme to an anticoagulant enzyme. The thrombin/thrombomodulin complex inhibits the coagulation cascade in at least two distinct ways. First, thrombin's binding to thrombomodulin potentiates thrombin-mediated activation of protein C. Activated protein C inactivates other procoagulant components of the coagulation cascade, such as Factors Va and VIIIa, which in turn inhibits the conversion of more prothrombin to thrombin. Thrombin-mediated activation of protein C is greatly enhanced when thrombin is bound to thrombomodulin i.e., the rate of protein C activation increases at least 1000-fold. Secondly, binding to thrombomodulin has direct anticoagulant effects such as the inhibition of thrombin-mediated conversion of fibrinogen to fibrin and thrombin-mediated activation and aggregation of platelets. Although normally an integral component of the endothelial cell membrane, thrombomodulin can be released from the membrane in the presence of sufficient detergent and retains the ability to bind to thrombin when in solution.

The preferred thrombomodulin analogs of this invention will protect against thrombus formation when administered systemically because they will inhibit the generation of thrombin without disturbing other coagulation parameters, ex., the activation and aggregation of platelets. Thus the use of soluble thrombomodulin analogs will be effective at preventing thrombus formation yet safer than native thrombomodulin and other antithrombotics known in the art.

Diseases in which thrombus formation plays a significant etiological role include myocardial infarction, disseminated intravascular coagulation, deep vein thrombosis, pulmonary embolism, septic shock, acute respiratory distress syndrome, unstable angina and other arterial and venous occlusive conditions. The thrombomodulin analogs of this invention are useful in all of these, as well as in other diseases in which thrombus formation is pathological. By useful it is meant that the compounds are useful for treatment, either to prevent the disease or to prevent its progression to a more severe state. The compounds of this invention also provide a safe and effective anticoagulant, for example, in patients receiving bioprostheses such as heart valves. These compounds may replace heparin and warfarin in the treatment of, for example, pulmonary embolism or acute myocardial infarction.

In particular these compounds would find a role in the prevention of deep vein thrombosis (DVT), for instance after surgery. The formation of blood clots in the leg is itself a non-fatal condition but is very closely tied to the development of pulmonary embolism (PE), which is difficult to diagnose and can be fatal. Despite the investigation and clinical use of several prophylactic regimens, DVT and the resulting PE remain a significant problem in many patient populations and particularly in patients undergoing orthopedic surgery. Existing prophylactic treatments such as heparin, warfarin and dextran typically reduce the incidence of DVT in orthopedic surgery patients from more than 50% in patients at risk receiving no prophylaxis to 25–30% among treated patients. There are serious side effects, primarily bleeding complications. Daily laboratory tests and adjustments in dosage are required to minimize bleeding episodes while retaining some efficacy. Based on the shortcomings of existing prophylactics, an antithrombotic which is effective at preventing DVT without predisposing the patient to bleeding could make a significant impact on patient recovery and well-being.

Angioplasty is a procedure frequently used for restoring patency in occluded arteries. Although patency may be restored, it is inherent in an angioplasty procedure that the endothelial lining of the artery is severely damaged, and blood clots frequently begin to form. Soluble thrombomodulin analogs administered in conjunction with angioplasty will prevent this deleterious side effect.

Many acute thrombotic and embolic diseases are currently treated with fibrinolytic therapy in order to remove the thrombus. The condition that has been most investigated is acute myocardial infarction (heart attack). Agents currently in use for treating acute myocardial infarction include streptokinase, tissue plasminogen activator and urokinase. Use of these agents can lead to serious bleeding complications. Patients who have had a thrombus removed by fibrinolytic therapy and in whom the blood flow has been restored frequently reocclude the affected vessel, i.e., a clot reforms. Attempts have been made to prevent the reocclusions by increasing the dose or time of treatment with a thrombolytic agent, but the incidence of bleeding then increases. Thus the therapeutic index for these drugs is narrow.

The use of thrombomodulin analogs provides protection against reocclusion and because its action is local, i.e., where thrombin is being generated or being released from a clot. Therefore, when used in combination with a thrombolytic agent whose dose can then be decreased, the risk of bleeding can be substantially reduced.

Administration of thrombomodulin analogs would be by a bolus intravenous injection, by a constant intravenous infusion or by a combination of both routes. Also, soluble thrombomodulin mixed with appropriate excipients may be taken into the circulation from an intramuscular site. Systemic treatment with thrombomodulin analogs can be monitored by determining the activated partial thromboplastin time (APTT) on serial samples of blood taken from the patient. The coagulation time observed in this assay is prolonged when a sufficient level of thrombomodulin is achieved in the circulation. However, this is a systemic measurement of efficacy, and the inventors have discovered that an effective dose of soluble TM analog does not necessarily effect the APTT. As used herein, a therapeutically effective dose is defined as that level of TM analog required to prevent formation of pathological clots. Dosing levels and regimens can be adjusted so that an adequate concentration of thrombomodulin is maintained as measured by, for example, the APTT assay.

Several methods are known for the detection and monitoring of thrombotic disease. Deep venous thrombosis can be detected, for example, by contrast venography, (Kerrigan, G. N. W., et al., (1974) *British Journal of Hematology*

26:469), Doppler ultrasound (Barnes, R. W. (1982) *Surgery Clinics in North America* 62:489–500), $^{125}$I-labeled fibrinogen uptake scanning (Kakkar, V. V., et al., (1972) *Archives of Surgery* 104:156, Kakkar, V. V., et al., (1970) *Lancet* i:540–542), impedance plethysmography (Bynum, L. J. et al., (1978) *Annals of Internal Medicine* 89:162), and thromboscintoscan (Ennis, J. T. and Elmes, R. J. (1977) *Radiology* 125:441). These methods are useful to monitor the efficacy of the methods and compositions described herein.

II. TM analogs.

A DNA sequence encoding the full-length native human thrombomodulin protein has been isolated (European Patent Application No. 88870079.6, which is incorporated herein by reference). The cDNA sequence encodes a 60.3 kDa protein of 575 amino acids, which includes a signal sequence of about 18 amino acids.

The sequences for bovine, mouse and human thrombomodulin exhibit a high degree of homology with one another. By analogy with other proteins, the structure of thrombomodulin can be presumptively divided into domains. The term "domain" refers to a discrete amino acid sequence that can be associated with a particular function or characteristic. The full length thrombomodulin gene encodes a precursor peptide containing the following domains:

| Approximate Amino Acid Position | Domain |
| --- | --- |
| −18–1 | Signal sequence |
| 1–226 | N-terminal domain |
| 227–462 | 6 EGF-like domains |
| 463–497 | O-linked Glycosylation |
| 498–521 | Stop Transfer Sequence |
| 522–557 | Cytoplasmic domain |

See C. S. Yost et al., (1983) *Cell,* 34:759–766 and D. Wen et al., (1987) *Biochemistry,* 26:4350–4357, both incorporated herein by reference. In comparison to native thrombomodulin, the preferred TM analogs of the present invention have been modified to embrace the 6 epidermal growth factor [EGF]-like domains plus or minus the O-linked glycosylation domain. Particularly preferred TM analogs are those that have the following characteristics: i) they are soluble in aqueous solution in the absence of detergents, ii) they retain activity after exposure to oxidants, and iii) when bound to thrombin, they potentiate the thrombin-mediated activation of protein C but have a reduced ability to inhibit the direct anti-coagulant activities of thrombin such as the conversion of fibrinogen to fibrin or the activation and aggregation of platelets. Assays for the latter two assays can be run on an automatic coagulation timer according to the manufacturer's specifications; Medical Laboratory Automation Inc. distributed by American Scientific Products, McGaw Park, Ill. (See also H. H. Salem et al., (1984) *J. Biol. Chem*, 259:12246–12251, which is incorporated herein by reference).

In a preferred embodiment, soluble TM analogs are oxidation resistant. This refers to analogs that retain activity after exposure to oxidants. Such analogs are described in detail in co-pending co-assigned U.S. Ser. No. 506,325 filed Apr. 9, 1990, incorporated herein by reference.

As used herein, a "soluble TM analog" is a TM analog which is soluble in an aqueous solution and can be secreted by a cell. For pharmacological administration, the soluble TM analog or an insoluble analog comprising the native cytoplasmic domain, may optionally be combined with phospholipid vesicles, detergents or other similar compounds well known to those skilled in the art of pharmacological formulation. The preferred TM analogs of the present invention are soluble in the blood stream, making the analogs useful in various anticoagulant and other therapies. These modifications do not significantly affect activities of native thrombomodulin such as affinity for thrombin or activity in protein C activation.

Two preferred analogs encompass the 6 EGF-like domains and are 4t/227–462 where the analog has the last four residues of the human tissue plasminogen activator signal peptide and 6h/227–462 where the 6h represents the last six residues of the hypodermin A signal sequence. More preferred are these analogs rendered oxidation resistant by substitution of the methionine at position 388 with leucine.

A. General Methods For Making TM Analogs

This invention embraces molecular genetic manipulations that can be achieved in a variety of known ways. The recombinant cells, plasmids, and DNA sequences of the present invention provide a means to produce pharmaceutically useful compounds wherein the compound, secreted from recombinant cells, is a soluble derivative of thrombomodulin.

Generally, the definitions of nomenclature and descriptions of general laboratory procedures used in this application can be found in J. Sambrook et al., *Molecular Cloning, A Laboratory Manula,* (1989) Cold Spring Harbor Laboratory, Cold Spring Harbor, N.Y. The manual is hereinafter referred to as Sambrook and is hereby incorporated by reference.

All enzymes are used according to the manufacturer's instructions.

Oligonucleotides that are not commercially available can be chemically synthesized according to the solid phase phosphoramidite triester method first described by S. L. Beaucage and M. H. Caruthers, (1981) *Tetrahedron Letts.,* 22(20):1859–1862 using an automated synthesizer, as described in D. R. Needham-VanDevanter et al., (1984) *Nucleic Acids Res.,* 12:6159–6168. Purification of oligonucleotides was by either native acrylamide gel electrophoresis or by anion-exchange HPLC as described in J. D. Pearson and F. E. Regnier, (1983) *J. Chrom.,* 255:137–149. Nucleotide sizes are given in either kilobases (kb) or base pairs (bp). These are estimates derived from agarose or acrylamide gel electrophoresis or from published DNA sequences.

The sequence of the cloned genes and synthetic oligonucleotides can be verified using the chemical degradation method of A. M. Maxam et al., (1980) *Methods In Enzymology,* 65:499–560. The sequence can be confirmed after the assembly of the oligonucleotide fragments into the double-stranded DNA sequence using the method of Maxam and Gilbert, supra, or the chain termination method for sequencing double-stranded templates of R. B. Wallace et al., (1981) *Gene,* 16:21–26. Southern Blot hybridization techniques were carried out according to Southern et al., (1975) *J. Mol. Biol.,* 98:503.

Embodiments of this invention require the creation of novel peptides and genes by in vitro mutagenesis. Target genes are isolated in intermediate vectors and cloned for amplification in prokaryotes such as *E. coli,* Bacillus or Streptomyces. Most preferred is *E. coli* because that organism is easy to culture and more fully understood than other species of prokaryotes. The Sambrook manual contains methodology sufficient to conduct all subsequently described clonings in *E. coli*. Strain MH-1 is preferred unless otherwise stated. All *E. coli* strains are grown on Luria broth (LB) with glucose, or M9 medium supplemented with glucose and acid-hydrolyzed casein amino acids. Strains with resistance to antibiotics were maintained at the drug concentrations described in Sambrook. Transformations were performed according to the method described by D. A. Morrison, (1977) *J. Bact.*, 132:349–351 or by J. E. Clark-Curtiss and R. Curtiss, (1983) *Methods in Enzymology*, 101:347–362, Eds. R. Wu et al., Academic Press, N.Y. Representative vectors include pBR322 and the pUC series which are available from commercial sources.

B. Gene Synthesis

The gene encoding native thrombomodulin has been isolated and sequenced from several species, both in its genomic form and as a cDNA (R. Jackman, et al., (1986) *PNAS* 83:8834–8838 and (1987) 84:6425–6429, both of which are herein incorporated by reference).

Publication of the full length DNA sequence encoding human thrombomodulin and thrombin facilitates the preparation of genes and is used as a starting point to construct DNA sequences encoding TM peptides. The peptides of the present invention are preferably soluble derivatives which lack the stop transfer sequence of TM in addition to having internal amino acid substitutions. Furthermore, these analogs are secreted from eukaryotic cells which have been transfected or transformed with plasmids containing genes which encode these polypeptides. Methods for making modifications, such as amino acid substitutions, deletions, or the addition of signal sequences to cloned genes are known. Specific methods used herein are described below.

The full length gene for thrombomodulin can be prepared by several methods. Human genomic libraries are commercially available. Oligonucleotide probes, specific to these genes, can be synthesized using the published gene sequence. Methods for screening genomic libraries with oligonucleotide probes are known. The publication of the gene sequence for thrombomodulin demonstrates that there are no introns within the coding region. Thus a genomic clone provides the necessary starting material to construct an expression plasmid for thrombomodulin using known methods.

A thrombomodulin encoding DNA fragment can be retrieved by taking advantage of restriction endonuclease sites which have been identified in regions which flank or are internal to the gene. (R. W. Jackman et al., (1987) Proc. Natl. Acad. Sci. USA., 84:6425-6429).

Alternatively, the full length genes can also be obtained from a cDNA bank. For example, messenger RNA prepared from endothelial cells provides suitable starting material for the preparation of cDNA. A cDNA molecule containing the gene encoding thrombomodulin is identified as described above. Methods for making cDNA banks are well known (See Sambrook, supra).

Genes encoding TM peptides may be made from wild-type TM genes first constructed using the gene encoding full length thrombomodulin. A preferred method for producing wild-type TM peptide genes for subsequent mutation combines the use of synthetic oligonucleotide primers with polymerase extension on a mRNA or DNA template. This polymerase chain reaction (PCR) method amplifies the desired nucleotide sequence. U.S. Pat. Nos. 4,683,195 and 4,683,202 describe this method. Restriction endonuclease sites can be incorporated into the primers. Genes amplified by the PCR reaction can be purified from agarose gels and cloned into an appropriate vector. Alterations in the natural gene sequence can be introduced by the techniques of in vitro mutagenesis or by use of the polymerase chain reaction with primers that have been designed to incorporate appropriate mutations.

The TM peptides described herein are secreted when expressed in eukaryotic cell culture. Secretion may be obtained by the use of the native signal sequence of the thrombomodulin gene. Alternatively, genes encoding the TM peptides of the present invention may be ligated in proper reading frame to a signal sequence other than that corresponding to the native thrombomodulin gene. For example, the signal sequence of t-PA, (see WO 89/00605 incorporated herein by reference) or of hypodermin A or B (see EP 326,419 which is incorporated hereby by reference) can be linked to the polypeptide (See Table 2). In the preferred embodiment of the present invention, use is made of the signal sequence of t-PA which contains the second intron of the human t-PA gene. The inclusion of the intron enhances the productivity of the adjacent structural gene.

With the analogs of this invention, those portions of the gene encoding the stop transfer and cytoplasmic domains of the carboxyl terminal region of the native thrombomodulin gene are deleted. Therefore, it is necessary to add a stop codon so that translation will be terminated at the desired position. Alternatively, a stop codon can be provided by the desired expression plasmid. Additionally a polyadenylation sequence is necessary to ensure proper processing of the mRNA in eukaryotic cells encoding the TM analog. Also, it may be necessary to provide an initiation codon, if one is not present, for expression of the TM peptides. Such sequences may be provided from the native gene or by the expression plasmid.

Cloning vectors suitable for replication and integration in prokaryotes or eukaryotes and containing transcription and translation terminators, initiation sequences, and promoters useful for regulation of the expression of TM peptides are described herein. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems.

C. Expression of TM Peptides in Prokaryotic Cells

In addition to the use of cloning methods in *E. coli* for amplification of cloned sequences it may be desirable to express TM analogs in prokaryotes. As discussed in greater detail below, the carbohydrate moieties of the mature protein are not essential for activity as a cofactor for the activation of protein C but do have an effect on the direct anticoagulant properties of the TM analogs as well as the molecule's half life in circulation. Expression of thrombomodulin analogs in *E. coli* has provided a useful tool for analysis of this issue. It is possible to recover a therapeutically functional protein from *E. coli* transformed with an expression plasmid encoding a soluble TM analog.

Methods for the expression of cloned genes in bacteria are well known. To obtain high level expression of a cloned gene in a prokaryotic system, it is essential to construct expression vectors which contain, at the minimum, a strong promoter to direct mRNA transcription termination. Examples of regulatory regions suitable for this purpose are the promoter and operator region of the *E. coli* β-galactosidase gene, the *E. coli* tryptophan biosynthetic pathway, or the leftward promoter from the phage lambda. The inclusion of selection markers in DNA vectors transformed in *E. coli* are useful. Examples of such markers include the genes specifying resistance to ampicillin, tetracycline, or chloramphenicol.

See Sambrook for details concerning selection markers and promoters for use in *E. coli*. In the described embodiment of this invention pUC19 is used as a vector for the subcloning and amplification of desired gene sequences.

D. Expression of TM Peptides in EukarVotic Cells

It is expected that those of skill in the art are knowledgeable in the expression systems chosen for expression of the desired TM peptides and no attempt to describe in detail the various methods known for the expression of proteins in eukaryotes will be made.

The DNA sequence encoding a soluble TM analog can be ligated to various expression vectors for use in transforming host cell cultures. The vectors typically contain marker genes and gene sequences to initiate transcription and translation of the heterologous gene.

The vectors preferably contain a marker gene to provide a phenotypic trait for selection of transformed host cells such as dihydrofolate reductase, metallo-thionein, hygromycin, or neomycin phosphotransferase. The nuclear polyhedral viral protein from *Autographa californica* is useful to screen transfected insect cell lines from *Spodoptera frugiperda* and *Bombyx mori* to identify recombinants. For yeast, Leu-2, Ura-3, Trp-1, and His-3 are known selectable markers (Gene (1979) 8:17–24). There are numerous other markers, both known and unknown, which embody the above scientific principles, all of which would be useful as markers to detect those eukaryotic cells transfected with the vectors embraced by this invention.

Of the higher eukaryotic cell systems useful for the expression of TM analogs, there are numerous cell systems to select from. Illustrative examples of mammalian cell lines include RPMI 7932, VERO and HeLa cells, Chinese hamster ovary (CHO) cell lines, WI38, BHK, COS-7, C127 or MDCK cell lines. A preferred mammalian cell line is CHL-1. When CHL-1 is used hygromycin is included as a eukaryotic selection marker. CHL-1 cells are derived from RPMI 7932 melanoma cells, a readily available human cell line. The CHL-1 cell line has been deposited with the ATCC according to the conditions of the Budapest Treaty and has been assigned #CRL 9446, deposited Jun. 18, 1987. Cells suitable for use in this invention are commercially available from the American Type Culture Collection. Illustrative insect cell lines include *Spodoptera fruqiperda* (fall Armyworm) and *Bombyx mori* (silkworm).

As indicated above, the expression vector, ex. plasmid, which is used to transform the host cell, preferably contains gene sequences to initiate the transcription and sequences to control the translation of the TM peptide gene sequence. These sequences are referred to as expression control sequences. When the host cell is of insect or mammalian origin, illustrative expression control sequences include but are not limited to the following: the retroviral long terminal repeat promoters ((1982) *Nature,* 297:479–483), SV40 promoter ((1983) *Science,* 222:524–527, thymidine kinase promoter (J. Banerji et al., (1982) *Cell,* 27:299–308), or the beta-globin promoter (P. A. Luciw et al., (1983) *Cell,* 33:705–716). The recipient vector nucleic acid containing the expression control sequences is cleaved using restriction enzymes and adjusted in size as necessary or desirable. This segment is ligated to a DNA sequence encoding at the TM peptide by means well known in the art.

When higher animal host cells are employed, polyadenylation or transcription termination sequences need to be incorporated into the vector. An example of a polyadenylation sequence is the polyadenylation sequence from SV40, which may also function as a transcription terminator.

Genes incorporated into the appropriate vectors can be used to direct synthesis of proteins in either transient expression systems or in stable clones. In the former case yields are low, but the experiments are quick. In the latter case it takes more time to isolate high producing clones. Different vectors may be used for the two different types of experiments. In particular, in the case of transient expression, sequences may be included within the plasmid that allow the plasmid to replicate to a high copy number within the cell. These sequences may be derived from virus such as SV40 (e.g. C. Doyle et al., (1985) *J. Cell Biol.,* 100:704–714) or from chromosomal replicating sequences such as murine autonomous replicating sequences (Weidle et al., (1988) *Gene,* 73:427–437). The vector for use in transient expression should also contain a strong promoter such as the SV40 early promoter (e.g., A. van Zonnenfeld et al., (1987) *Proc. Natl. Acad. Sci. USA.,* 83:4670–4674) to control transcription of the gene of interest. While transient expression provides a rapid method for assay of gene products, the plasmid DNA is not incorporated into the host cell chromosome. Thus, use of transient expression vectors does not provide stable transfected cell lines. A description of a plasmid suitable for transient expression is provided by A. Aruffo & B. Seed, (1987) *Proc. Natl. Acad. Sci. USA.,* 84:8573–8577.

TM analogs may alternatively be produced in the insect cell lines described above using the baculovirus system. This system has been described by V. A. Luckow and M. D. Summers (1988) *Bio/Technology,* 6:47–55. Generally, this expression system provides for a level of expression higher than that provided by most mammalian systems. The baculovirus infects the host insect cells, replicates its genome through numerous cycles, and then produces large amounts of polyhedron crystals. The polyhedron gene can be replaced with a TM peptide gene. The polyhedron promoter will then make large amounts of analog protein following infection of the culture host cell and replication of the baculovirus genome. The non-secreted gene product is harvested from the host 3–7 days post infection. Alternatively, the TM peptide may be secreted from the cells if appropriate signal sequences are present on the protein.

The host cells are competent or rendered competent for transfection by various means. There are several well-known methods of introducing DNA into animal cells. These include: calcium phosphate precipitation, DEAE-dextran technique, fusion of the recipient cells with bacterial protoplasts containing the DNA, treatment of the recipient cells with liposomes containing the DNA, electroporation and microinjection of the DNA directly into the cells. See, B. Perbal, *"Practical Guide to Molecular Cloning,"* 2nd edition, John Wiley & Sons, New York and Wigler, et al., (1987) *Cell,* 16:777–785.

E. Culturing Cells

It is preferred that the host cell is capable of rapid cell culture and able to appropriately glycosylate expressed gene products. Cells known to be suitable for dense growth in tissue culture are particularly desirable and a variety of invertebrate or vertebrate cells have been employed in the art, both normal and transformed cell lines.

The transfected cells are grown up by means well known in the art. For examples, see Biochemical Methods in *Cell Culture and Virology*, Kuchler, R. J., Dowden, Hutchinson and Ross, Inc. (1977). The expression products are harvested from the cell medium in those systems where the protein is secreted from the host cell or from the cell suspension after disruption of the host cell system by, e.g., mechanical or enzymatic means, which are well known in the art.

F. Purification of TM Analogs

It is preferred that the TM peptides of this invention be secreted by cultured recombinant eukaryotic cells. The TM analogs are produced in serum-free or serum supplemented media and are secreted intact. If prokaryotic cells are used, the TM analogs may be deposited intracellularly. The peptides may be fully or partially glycosylated or non-glycosylated. Following the growth of the recombinant cells and concomitant secretion of TM analogs into the culture media, this "conditioned media" is harvested. The conditioned media is then clarified by centrifugation or filtration to remove cells and cell debris. The proteins contained in the clarified media are concentrated by adsorption to any suitable resin such as, for example, Q Sepharose or metal chelators, or by use of ammonium sulfate fractionation, polyethylene glycol precipitation, or by ultrafiltration. Other means known in the art may be equally suitable. Further purification of the TM analogs can be accomplished in the manner described in Galvin, J. B., et al., (1987) *J. Biol. Chem.*, 262:2199–2205 and Salem, H. H. et al., (1984) *J. Biol. Chem.*, 259:12246–12251 and in the manner described in the embodiment disclosed herein. The purification of TM analogs secreted by cultured cells may require the additional use of, for example, affinity chromatography, ion exchange chromatography, sizing chromatography or other protein purification techniques.

Recombinant TM analogs may be produced in multiple conformational forms which are detectable under nonreducing chromatographic conditions. Removal of those species having a low specific activity is desirable and is achieved by a variety of chromatographic techniques including anion exchange or size exclusion chromatography. Recombinant TM analogs may be concentrated by pressure dialysis and buffer exchanged directly into volatile buffers (e.g., N-ethylmorpholine (NEM), ammonium bicarbonate, ammonium acetate, and pyridine acetate). In addition, samples can be directly freeze-dried from such volatile buffers resulting in a stable protein powder devoid of salt and detergents. In addition, freeze-dried samples of recombinant analogs can be efficiently resolubilized before use in buffers compatible with infusion (e.g., phosphate buffered saline). Other suitable buffers might include hydrochloride, hydrobromide, sulphate acetate, benzoate, malate, citrate, glycine, glutamate, and aspartate.

G. Oxidation Resistant TM analogs.

Native thrombomodulin is susceptible to oxidation and when oxidized loses its ability to promote the activation of protein C. Many of the disease conditions requiring anticoagulation are also associated with high levels of toxic oxygen radicals, which can inactivate biomolecules and cause significant tissue damage. Examples of these conditions are reperfusion injury associated with myocardial infarction, DIC associated with septicemia, and alveolar fibrosis associated with adult respiratory distress syndrome. (See, Otani, H., et al., (1984) *Circ. Res.* 55:168–175, Saldeen, T., (1983) *Surg. Clin. N. A.* 63(2):285–304, and Idell, S., et al., (1989) *J. Clin. Inv.* 84:695–705.) In addition, any wound, such as occurring in surgical procedures, involves the influx of activated monocytes, polymorphonuclear leukocytes, etc. which can create toxic oxygen species as well as releasing a host of proteolytic enzymes, such as elastase. The connection between endothelial cell damage, inflammation and thrombosis has long been recognized (See *The Molecular and Cellular Biology of Wound Repair*, ed. Clark, R. A. F. and P. M. Henson 1988, for example). Thrombomodulin is subject to inactivation by exposure to toxic oxygen species and that this is expected to have a significant role in many pathogenic states.

Methods for rendering amino acids, specifically methionines, resistant to oxidation are well known in the art. It is possible to chemically modify thiol groups with iodoacetic acid, for example, to form oxidation resistant sulphonium (Gundlach, H. G., et al., (1959) *J. Biol. Chem.* 234:1754). A preferred method is by removing the susceptible amino acid or replacing it with one or more different amino acids that will not react with oxidants. The amino acids leucine, alanine and glutamine would be particularly preferred amino acids because of their size and neutral character. Two methionines of thrombomodulin subject to oxidation are those located at residue 291 and 388. If only one methionine is to be blocked or eliminated, it is preferred that it be the residue at position 388.

Methods by which amino acids can be removed or replaced in the sequence of a protein are well known. Genes that encode a peptide with an altered amino acid sequence can be made synthetically, for example. A preferred method is the use of site-directed in vitro mutagenesis. Site-directed mutagenesis involves the use of a synthetic oligodeoxyribonucleotide containing a desired nucleotide substitution, insertion or deletion designed to specifically alter the nucleotide sequence of a single-strand target DNA. Hybridization of this oligonucleotide, also called a primer, to the single-strand template and subsequent primer extension produces a heteroduplex DNA which when replicated in a transformed cell, will encode a protein sequence with the desired mutation.

To determine the resistance to loss of thrombomodulin activity due to oxidation, the test material (100–250 μg/ml) is first incubated with an oxidant such as, for example, chloramine-T, hydrogen peroxide at 5–10 mM chloramine-T or 200–1000 mM hydrogen peroxide in a buffer of 0.2% N-ethylmorpholine and 0.008% Tween 80 at pH 7.0 for 20 minutes at room temperature. After such oxidant exposure, the test material is evaluated using one of the bioactivity assays described below, specifically for the ability to act as a cofactor for the activation of protein C. Those mutant TM analogs that retain at least 60%, and preferably 90%, of activity they had prior to exposure to oxidants are considered to be oxidation resistant as compared to wild-type (non-mutant) TM analog or native thrombomodulin.

H. Laboratory Assays for Measuring TM Activity.

A number of laboratory assays for measuring TM activity are available. Protein C cofactor activity can be measured in the assay described by Salem, et al., (1984) *J. Biol. Chem.* 259(19):12246–12251 and Galvin, et al., (1987) *J. Biol.*

*Chem.* 262(5):2199–2205. In brief, this assay consists of two steps. The first is the incubation of the test TM analog with thrombin and protein C under defined conditions (see Examples below). In the second step, the thrombin is inactivated with hirudin or antithrombin III and heparin, and the activity of the newly activated protein C is determined by the use of a chromogenic substrate, whereby the chromophore is released by the proteolytic activity of activated protein C. This assay is carried out with purified reagents.

Alternatively the effect of a TM analog can be measured using plasma in clotting time assays such as the activated partial thromboplastin time (APTT), thrombin clotting time (TCT) and/or prothrombin time (PT). These assays distinguish between different mechanisms of coagulation inhibition, and involve the activation of protein C. Prolongation of the clotting time in any one of these assays demonstrates that the molecule can inhibit coagulation in plasma.

The above assays are used to identify soluble TM analogs that are able to bind thrombin and to activate protein C in both purified systems and in a plasma milieu. Further assays are then used to evaluate other activities of native thrombomodulin such as inhibition of thrombin catalyzed formation of fibrin from fibrinogen (Jakubowski, et al., (1986) *J. Biol. Chem.* 261(8):3876–3882), inhibition of thrombin activation of Factor V (Esmon, et al., (1982) *J. Biol. Chem.* 257:7944–7947), accelerated inhibition of thrombin by antithrombin III and heparin cofactor II (Esmon, et al., (1983) *J. Biol. Chem.* 258:12238–12242), inhibition of thrombin activation of Factor XIII (Polgar, et al., (1987) *Thromb. Haemostas.* 58:140), inhibition of thrombin mediated inactivation of protein S (Thompson and Salem, (1986) *J. Clin. Inv.* 78(1):13–17) and inhibition of thrombin mediated platelet activation and aggregation (Esmon, et al., (1983) *J. Biol. Chem.* 258:12238–12242).

In the present invention, the TM analogs do not have all activities equal to that of native thrombomodulin. For example, if one compares an amount of a TM analog of the present invention with an equivalent amount of native thrombomodulin (as measured in units of protein C cofactor activity, defined below) the TM analog will have at least a 20% reduction, and preferably a 50% reduction in its ability to inhibit thrombin-mediated conversion of fibrinogen to fibrin compared to the native thrombomodulin.

I. Methods for Altering the Glycosylation of TM Analogs.

Carbohydrate substituents on proteins can affect both biological activity and circulating half-life. In order to make the TM analogs of the present invention, O-linked glycosaminoglycan carbohydrate such as is found in the native thrombomodulin protein, must be absent. There are numerous ways for accomplishing this objective. One method would be the treatment of the O-linked carbohydrate containing protein with a glycanase known to specifically degrade sulfated glycosaminoglycans, such as chondroitinase ABC or hyaluronidase. This method is described in Bourin, M, et al., (1988) *JBC* 263(17):8044–8052, which is herein incorporated by reference.

A second method for eliminating the O-linked carbohydrate is by introducing site directed mutations into the protein. The attachment of glycosaminoglycans is directed by the consensus recognition sequence of amino acids X-serine-glycine-X-glycine-X (Bourdon, M. A., et al., (1987) *PNAS, U.S.A.* 84:3194–3198) where X is any amino acid. The recognition sequence for other types of O-linked sugars is threonine/serine-X-X-proline. The O-linked domain of thrombomodulin has one potential glycosaminoglycan addition site (aa 472) and three other potential O-linked carbohydrate addition sites (aa 474, 480 and 486). Any change introduced into the nucleotide sequence that removes or changes the identity of any one or more of the amino acids in this recognition sequence will eliminate the potential O-linked carbohydrate attachment site. Methods of introducing site directed mutations into a nucleotide sequence are described above.

A preferred method of eliminating O-linked carbohydrate from a TM analog is by making an analog peptide that does not include the amino acids that are considered to be the O-linked domain, i.e., amino acids 468 through 485 of the native thrombomodulin gene sequence as shown in Table 1. Methods of accomplishing this are well known in the art and have been described above.

The circulating half-life of a protein can be altered by the amount and composition of carbohydrate attached to it. The TM analogs of the present invention contain both O-linked and N-linked carbohydrate. In addition to the potential glycosylation sites discussed above there are potential N-linked sites at amino acids 364, 391 and 393 and potential O-linked sites at amino acids 319, 393 and 396. Methods of altering carbohydrate composition in addition to those described above are: 1) expression of the TM analog gene in bacteria such *E. coli*, which does not have the cellular mechanisms necessary to glycosylate mammalian proteins, 2) expression of the TM analog gene in various eukaryotic cells, as each has its own characteristic enzymes that are responsible for the addition of characteristic sugar residues, and 3) treatment with chemicals such as hydrofluoric acid. Hydrofluoric acid, for example, chemically digests acid and neutral pH sugars while leaving intact basic sugars such as N-acetyl glucosamines and, under certain conditions, galactosamines.

J. Formulation and Use of Thrombomodulin Analogs

The soluble TM analogs described herein may be prepared in a lyophilized or liquid formulation. The material is to be provided in a concentration suitable for pharmaceutical use as either an injectable or intravenous preparation.

These compounds can be administered alone or as mixtures with other physiologically acceptable active materials, such as antibiotics, other anti coagulants, one-chain t-PA, or inactive materials, or with suitable carriers such as, for example, water or normal saline. The analogs can be administered parenterally, for example, by injection. Injection can be subcutaneous, intravenous or intramuscular.

These compounds are administered in pharmaceutically effective amounts and often as pharmaceutically acceptable salts, such as acid addition salts. Such salts can include, e.g., hydrochloride, hydrobromide, phosphate, sulphate, acetate, benzoate, malate, citrate, glycine, glutamate, and aspartate, among others. The analogs described herein may display enhanced in vivo activity by incorporation into micelles. Methods for incorporation into ionic detergent micelles or phospholipid micelles are known.

An antithrombotic agent can be prepared using the soluble TM analogs described herein and can consist of a completely purified analog alone or in combination with a thrombolytic agent as described above. Compounds of the present invention which are shown to have the above recited physiological effects can find use in numerous therapeutic applications such as, for example, the inhibition of blood clot formation. Thus, these compounds can find use as therapeutic agents in the treatment of various circulatory disorders, such as, for example, coronary or pulmonary embolism, strokes, as well as the prevention of reocclusion following thrombolytic therapy, and these compounds have utility in the cessation of further enlargement of a clot during an infarction incident. Further, the compounds disclosed can be useful for treatment of systemic coagulation disorders such as disseminated intravascular coagulation (DIC), which is often associated with septicemia, certain cancers and toxemia of pregnancy.

These compounds can be administered to mammals for veterinary use, such as with domestic animals, and for clinical use in humans in a manner similar to other therapeutic agents, that is, in a physiologically acceptable carrier. In general, the administration dosage for the TM analog will range from about 0.0002 to 5000 µg/kg, and more usually 0.02 to 500 µg/kg of the host body weight. These dosages can be administered by constant infusion over an extended period of time, until a desired circulating level has been attained, or preferably as a bolus injection.

EXAMPLES

EXAMPLE 1. Isolation and expression of TM analog sequences

A. Cloning

Genes for producing recombinant thrombomodulin analog peptides were isolated as described in copending applications U.S. Ser. No. 345,372, filed Apr. 28, 1989, U.S. Ser. No. 406,941, filed Sep. 13, 1989, and PCT Serial No. 90/00955, filed Feb. 16, 1990, each herein incorporated by reference. Briefly, human DNA was used to isolate a gene encoding the 6 EGF-like domains of thrombomodulin corresponding to amino acids 227–462 as well as other portions of the thrombomodulin peptide. (See Table 1). This DNA was isolated from fetal liver according to the method of Blin, N and DW Stafford, (1976) Nucleic Acids Res. 3:2302. The DNA was then used as a template in a polymerase chain reaction with synthetically derived primers selected to embrace the desired regions (See Tables 3 & 4).

i. Isolation of genes encoding amino acids 227–462

The following steps provide a means to obtain a DNA insert encoding amino acids (aa) 227–462 and uses primers #1033 and #1034 (See Table 3). It is understood that by modifying the procedures set forth below by using alternative primers, other soluble TM analogs can be obtained.

The sequence of the #1033 and #1034 primers correspond to the 5' and 3' ends of the desired domain, but they have been modified so that they contain a BamHI site. A termination codon (TGA) was introduced following base 1586. The polymerase chain reaction was run under the conditions described by Saiki, et al., (1988) Science 320:1350–1354, except that the initial temperature of annealing was 37° C. After 10 cycles, the annealing temperature was raised to 45° C. for the remaining 30 cycles. An aliquot of the reaction products was separated on a 5% polyacrylamide gel and visualized by ethidium bromide staining. A band of the predicted size (700 bp) could clearly be seen. Alternatively one can sequence this band or hybridize it to an internal probe to confirm its identity.

ii. Isolation of genes encoding other regions of thrombomodulin

The polymerase chain reaction as herein described was used in the same manner to isolated additional fragments of thrombomodulin corresponding to the regions listed in Table 4. In particular, these regions embrace one or more of the EGF-like domains and the O-linked glycosylation domain. The sequences of the primers selected to produce the desired regions are shown in Table 3.

iii. Cloning plasmids containing the thrombomodulin analog genes

The remainder of the polymerase chain reaction mixture described above (i) was restricted with BamHI, separated on a 5% polyacrylamide gel, and the 700 bp band was excised and eluted. It was ligated to pUC19 that had been restricted with BamHI and the new plasmid was transformed into E. coli strain DH5-alpha. Recombinant colonies were selected on a medium containing ampicillin and 5-bromo-4-chloro-3-indolyl-B-D-galactoside. White colonies were picked onto a grid and hybridized by the Grunstein-Hogness technique with a synthetically derived gene corresponding to aa 283–352 of thrombomodulin that had been cut out of a cloning plasmid (pTM2.1) with EcoRI and HindIII before labelling with $^{32}P$ by random priming (Boehringer Mannheim).

After exposing the filters to X-ray, film the one colony that hybridized to the pTM2.1 probe was selected and a culture grown up. DNA was extracted and analyzed by restriction with either BamHI or BglII to confirm the presence of an insert with the correct restriction map. The excised insert was also transferred to nitrocellulose and analyzed by hybridization with labelled pTM2.1. Both methods confirmed that the 700 bp insert contained the coding sequence for the 6 EGF-like domains of thrombomodulin. The insert was sequenced to verify that no mutations had been inadvertently introduced during the PCR. The plasmid containing the desired gene fragment is named pUC19pcrTM7.

B. Expression of TM

1. Construction of AcNPV Transfer Vectors

The transfer vectors described below are also described in copending application U.S. Ser. No. 345,372. The transfer vectors contain the Hypodermin A signal sequence from *Hypoderma lineatum*.

i. pHY1 and pSC716.

Oligomers containing the Hypodermin A signal sequence, a translation initiation codon, a BglII cloning site, a BamHI 5' overhand and a Kpnl 3' overhang, COD#1198 and COD#1199 (see Table 2), were annealed and cloned into pSC654, a pUC19 derivative, creating pHY1. Plasmid pHY1 was restricted with BamHI and EcoRI, releasing the hypodermin A signal sequence. This sequence was then ligated to pSC714 to create the vector pSC716. Plasmid pSC714 is a derivative of pVL1393, obtained from Summers, et al. The only difference between the two is that in pSC714, one of the BglII sites has been destroyed.

ii. Construction of pHY101

The BamHI fragment from pUC19pcrTM7 (see Aiii above) was cloned into the BglII site of pHY1 and the orientation was chosen such that the hypodermin A signal sequence was adjacent to amino acid 227. This plasmid is pHY101.

iii. Construction of the AcNPV transfer vector pTMHY101.

Plasmid pHY101 was treated with BamHI/EcoRI which releases the Hypodermin A signal sequence linked to the TM analog coding sequence. Shuttle vector pVL1393 contains a partially deleted AcNPV polyhedrin gene and unique BamHI and EcoRI cloning sites. The BamHI/EcoRI fragment from pHY101 was inserted downstream of the polyhedrin promoter, thus creating a plasmid, pTMHY101, in which the hybrid gene was under the control of the polyhedrin promoter.

iv. Construction of other ACNPV transfer vectors.

Transfer plasmids containing other TM analog gene sequences were constructed using a strategy similar to that outlined above. Fragments from the cloning plasmids described above were cloned into pSC716 in frame so that the TM analog gene sequence was fused to the hypodermin A signal sequence. The TM gene sequences are listed in Table 4.

v. Production of pure phage stocks

Cell transfection was done using a calcium phosphate precipitation technique modified for insect cells according to Summers and Smith. Briefly, a T25 flask was seeded with $2 \times 10^6$ Sf9 cells, and the cells were allowed to attach for one hour at room temperature. Two ugs of transfer vector, for example pTHR28, and 1 ug of AcNPV DNA were coprecipitated in calcium phosphate and incubated with the cells for 4 hours. The cells were rinsed and re-fed with growth media, then placed in a 28° C. incubator for 3–4 days. During this incubation, the cells produce both recombinant and non-recombinant virus which accumulate in the growth media. This media, containing a mixed viral stock, was assayed for the presence of protein C cofactor activity (see below).

Recombinant viruses were detected by plaque assay. The transfection stocks were diluted ($10^{-4}$, $10^{-5}$, and $10^{-6}$) and plated 4–7 days post-transfection. Occlusion negative (recombinant) plaques were picked 7 days after plating and replated ($10^{-1}$, $10^{-2}$, and $10^{-3}$ dilution). After another 7 days, the plates showed 100% pure occlusion negative recombinant plaques. A single pfu from each was selected for production. A high titer viral stock was grown by infecting 5 mls of Sf9 cells ($1 \times 10^6$/ml in Excell 400 medium (JR Scientific)) with a single pfu, growing for 4–5 days. A portion of this stock was then diluted 1:50–1:100 into Sf9 cells grown to mid-log phase to produce a protein stock.

2. Production of Human TM Analogs in Mammalian Cells i. Mammalian expression vectors for TM analogs This example provides a mammalian expression vector comprising the analog genes of Example 1, A. The genes are operably linked to the signal sequence of human tissue plasminogen activator (See Table 2). The expression plasmid, pPA124, contains a promoter contained within the three copies of the long terminal repeats derived from Harvey Sarcoma virus for the expression of cloned genes. This plasmid was derived from pPA119, and pSC672, both described in detail in co-pending U.S. Ser. No. 251,159, filed Sep. 29, 1988, incorporated herein by reference. A BglII - BclI fragment containing the SV40 polyadenylation region was isolated from pSC672. This fragment was cloned into pPA119 which had been digested with BflII and BclI. In the resulting plasmid, pPA124, both the BflII and BclI sites remained intact. Plasmid pPA124 contains the t-PA signal sequence adjacent to an appropriate restriction site and this signal sequence also contains the second intron of the human t-PA gene.

The gene encoding the soluble TM analog was removed from pUC19pcrTM7 by treatment with BamHI and ligated to pPA124 that had been treated with BglII. Transformants were screened for the presence of the insert in the correct orientation, that is in which the t-PA signal sequence was linked to the 5' end of the thrombomodulin insert encoding an open reading frame. This plasmid, pTM101, was then digested with ClaI and ligated to a ClaI fragment containing the dhfr gene under the control of the SV40 promoter. The ClaI fragment is described in WO88/02411 at page 26. Transformants were screened for the presence of this dhfr cassette and then the orientation relative to the plasmid was determined by restriction mapping (pTM103).

Plasmid pTM103, containing the dhfr sequence in the divergent direction to the thrombomodulin sequence, was treated with BclI and a DNA fragment encoding a gene providing hygromycin resistance on a BamHI fragment was ligated into the plasmid. Clones were selected, after transformation into *E. coli* strain DH5α, by their ability to grow on plates containing both ampicillin and hygromycin B. The orientation of the hygromycin B gene relative to the plasmid was determined by restriction mapping. One plasmid, pTM108, in which the hygromycin B gene lies in the opposite orientation to the TM gene, was grown up in culture. This plasmid has the sequences encoding the TM analog under the control of the triple LTR promoter, with both a gene that confers hygromycin B resistance and one that encodes dhfr present on the plasmid. A similar expression plasmid, pTHR13, also contains the t-PA signal sequence operably linked to the sequence encoding the 6 EGF-like domains both under the control of the cytomegalovirus promoter. This plasmid contains the M13 origin of replication making it useful for site directed in vitro mutagenesis, described below. The thrombomodulin sequence was linked to the tissue plasminogen activator signal sequence, ensuring its secretion. The TM analog produced by both these plasmids, 4t/227–462, is comprised of the 6 EGF-like domains of thrombomodulin with an additional 4 amino acids on the N-terminal end that are the result of processing of the t-PA signal peptide.

ii. Transfection, selection and amplification of stable mammalian clones.

For the transfection, 10 μg of pTM108 was mixed with Lipofectin reagent (Bethesda Research Laboratories) and added to a monolayer of $10^5$ CHL-1 host cells in 6-well plates. Forty-eight hours after transfection, a known number of cells were plated onto selective media. Resistance to hygromycin B was used as the selection marker. CHL-1 cells transfected with the bacterial hygromycin B gene can survive growth in 0.3 mg/ml hygromycin B.

The transfection or selection frequency was $2/10^3$ and was determined as the number of colonies arising after selection, divided by the total number of cells plated. The culture supernatant was shown to contain 1.5 U/ml TM activity after 24 hours in contact with the cells.

A population of cells resistant to the first selection conditions were then subjected to a second round of selective pressure. Either 100 nM or 500 nM methotrexate (MTX) was added to the growth medium to select for transfectants that expressed the dhfr gene. Only clones which had amplified the dhfr gene would be able to grow in this high level of MTX. In the process of gene amplification, other plasmid sequences will be co-amplified with the dhfr gene and thus lead to increased gene expression of the non-selectable gene as well. Resistant clones were apparent after 5 to 6 weeks. Individual clones resistant to these levels of MTX were isolated and assayed. A culture after selection in 100 nM MTX was shown to produce 4.9–14.7 U per ml of protein C activating activity (see below). A pooled population was plated into a ten-fold greater concentration of MTX (1 μM or 5 μM). Clones were again recovered from this selection step and assayed. At each step clones were shown to produce and secrete TM analog into the culture medium.

C. Site-directed Mutagenesis

The 6 EGF-like domains region of native thrombomodulin has two methionine residues, one at position 291 and one at position 388. (See Table 1). Site-directed in vitro mutagenesis was used to convert either or both of these methionines to other amino acids. Site-directed mutagenesis uses a synthetic DNA sequence containing a desired nucleotide substitution, insertion or deletion to specifically alter the nucleotide sequence of a single-stranded template DNA. Hybridization of this synthetic DNA to the template and subsequent primer extension produces a heteroduplex DNA capable of cell transformation to yield the desired mutation. A diagram depicting this process is shown in FIG. 1.

A plasmid for making single stranded DNA copies, pTHR14, was constructed by ligating the F1 origin of replication contained on an AseI-ScaI fragment into an insect cell transfer vector, pTMHY101, previously digested with NdeI and ScaI. Plasmid pTMHY101 contains a gene sequence that produces a peptide corresponding to the 6 EGF-like domains of thrombomodulin, amino acids 227–462 and is described above. pTMHY101 is described in copending application U.S. Ser. No. 345,372 as well as B(1)(iii) above.

Specific mutagenizing oligonucleotide primers were synthesized and used with the MUTATOR™—DNA Polymerase III Site-directed Mutagenesis Kit (Catalogue #200500, Stratagene, La Jolla, CA), except as otherwise noted to prime second strand synthesis and create thrombomodulin analog genes with either one or both of the methionines changed to a non-oxidizable amino acid. Primers directing conversion to the preferred amino acids leucine, glutamine or alanine are shown in Table 5. Also included in these primers are substitutions in the nucleotide sequence that add a unique restriction enzyme site useful as a diagnostic for successful mutagenesis but which do not necessarily change the corresponding amino acid sequence. The nucleotide substitutions are underlined in the primers shown in Table 5. For example, in plasmid pTHR28 the methionine at position 388 in the native thrombomodulin protein was replaced with leucine, and in the process a unique PvuII site was introduced. It is understood that other substitute non-oxidizable amino acids would be equally useful in this invention.

Purified single-stranded DNA templates were prepared using the procedure described by Bio-Rad (Muta-Gene Phagemid in vitro Mutagenesis, Instruction Manual, Cat. no. 170-3576, pages 33–34) although other procedures known in the art would be equally suitable.

The 5' terminus of each mutagenizing primer was phosphorylated by incubating 0.5 ng/ul of primer in a solution containing 2 mM rATP, 0.4 U/ul polynucleotide kinase in annealing buffer (20 mM Tris-HCl pH 7.5, 8 mM $MgCl_2$ and 40 mM NaCl) at 37° C. for 30 minutes. The reaction was heat inactivated by incubating the mixture at 65° C. for 15 minutes. Phosphorylation increases the rate of successful mutation. The phosphorylated primer was annealed to the single-stranded template by heating 100 ng of template and 2.5 ng of primer in 25 ul of annealing buffer to 65° C. for 5 minutes then allowing the mixture to cool and anneal at room temperature for 10 minutes. Double stranded DNA was made by primer extension essentially as described by Tsurushit, N., et al., (1988) *Gene* 62:135–139 and O'Donnell, M. E., et al., (1985) *J. Biol. Chem.* 260:12875–12883. Briefly, the template/primer mixture was diluted (1:1) with 10% annealing buffer plus 80 ug/ml bovine serum albumin, 2.5 mM dithiothreitol, 0.25 mM mixed dNTPs, 2 mM rATP and 1% glycerol plus 1 ug of single-stranded DNA binding protein. The reaction was incubated for 5 minutes at room temperature to allow the binding protein to coat the single-strand DNA template. DNA polymerase III holoenzyme (*E. coli*, 1.7 ul of 50 U solution) was added, and the reaction was incubated at 30° C. for 10 minutes. T4 DNA ligase was added (0.5 ul, 2 Weiss units) and the reaction was further incubated for 5 minutes at 30° C. This mixture was used to transform *E. coli* and properly mutated clones were selected by restriction digest pattern.

This same process can be used to make mutants that can be expressed in mammalian cells using, for example, pTR13 (described above) which has an M13 origin of replication for making single stranded DNA templates.

D. Production and purification of recombinant protein.

T25 flasks were seeded at a density of $2 \times 10^6$ Sf9 cells in 5 ml TMN-FH media plus 10% FBS or Excell 400, then infected with an isolated recombinant plaque from Part B or C above. Viral stocks were collected after three days. Flasks (30–100 ml shaker flasks or 100–300 ml spinner flasks) were seeded with cells (1–1.8×106/ml) and infected with aliquots of the viral stock equal to ⅕₀th to 1¹⁄₁₀₀th of the final volume. The infected cell cultures were grown for four days before harvesting the conditioned media containing recombinant oxidation resistant TM analog protein.

The TM analogs were purified from conditioned media by removal of cell debris, followed by five chromatography steps: 1) Q Sepharose, 2) thrombin affinity, 3) gel filtration, 4) anion exchange, and 5) a second gel filtration step. The gel filtration steps effect an exchange of buffers. All chromatography steps were performed at 4° C.

i. Materials

Some of the chromatographic resins were purchased from commercial sources. Q Sepharose and Sephadex G25 was purchased from Sigma (St. Louis, MO), and Mono Q 5/5TM from Pharmacia LKB (Piscataway, NJ).

DFP-thrombin agarose was prepared approximately as follows: 360 mg of bovine thrombin in 100 ml of 20 mM Na phosphate, pH 7.5 was added to approximately 100 ml of a 50% Affigel 10 resin slurry and mixed overnight at 4° C. The Affigel 10 was prepared for use as described by the manufacturer and equilibrated with the load buffer. Residual active esters were blocked by the addition of 100 ml of 0.1 M glycine (pH 5.6) for one hour at 4° C. The gel was then equilibrated with 30 mM Tris-HCl, 2 M NaCl, pH 7.5, and 20 μl of DFP was added to give a final concentration of about 1 mM DFP. After 16 hrs of mixing at 4° C. an additional 6 μl of DFP was added and mixing continued for 4 additional hours. The resin was then washed with 20 mM Tris-HCl, 2 M NaCl pH 7.5 and stored at 4° C.

Thrombin activity was measured using the Kabi S-2238 substrate and indicated that >86% of the thrombin was removed from the solution, and presumably coupled to the resin, giving a final concentration of about 6 mg of thrombin per ml of resin. The enzymatic activity of the DFP treated resin was <1% of the starting activity.

ii. Production of pure TM analog peptide.

Conditioned media was harvested and clarified by centrifugation at 1400×g for 10 minutes. The pH was adjusted from about 6.0 to about 5.2 with glacial acetic acid. The adjusted media was then loaded onto a column of Q Sepharose resin. The column had previously been equilibrated with about four column volumes of wash buffer 1 (117 mM Na acetate, 0.02% $NaN_3$ pH 5.0). After loading, the column was washed with wash buffer 1 followed by wash buffer 2 (25 mM Na acetate, 0.1 M NaCl pH 5.0) then the oxidation resistant TM analog was eluted with wash buffer 2 containing 0.3 M NaCl, pH 5.0.

Column fractions containing activity as measured in the protein C activation assay (see above) were pooled, then diluted with of 0.3 M NaCl, 20 mM Tris-HCl, 0.5 mM $CaCl_2$, 0.02% $NAN_3$, pH 7.5. The pH of the diluate was measured and adjusted to about 7.5 with NaOH. The ionic strength of the pool was about the ionic strength of a solution of 0.3 M NaCl. This adjusted pool was loaded overnight by gravity onto a thrombin agarose column pre-equilibrated with the same buffer used to dilute the conditioned media. The column was washed with diluent buffer, and the TM analog was removed from the matrix with 1.5 M GuHCl, 2.0 M NaCl, 20 mM Tris HCl, 1 mM Na EDTA, 0.02% $NAN_3$, pH 7.5.

The substantially pure TM analog was applied to a Sephadex G25 column and recovered in 0.2% N-ethylmorpholine acetate (NEM) pH 7.0. This step removes GuHCl and NaCl.

TM analog collected from the Sephadex G25 column was applied to a Mono Q column (Pharmacia, 10 micron particles, quarternary amine) pre-equilibrated with 0.2% N-ethylmorpholine (NEM). pH7.0. After washing with this buffer the various forms were separated using a gradient of 0 to 0.4 M NaCl. Samples of each fraction were evaluated on an SDS-PAGE gel under non-reducing conditions. SDS Polyacrylamide Gel Electrophoresis was performed by the method of Laemmli using 3.3% acrylamide in the stacking and 12.5% acrylamide in the running gel. Nonreduced samples were diluted in Laemmli sample solubilization buffer (50 mM Tris-HCl, pH 6.8, 25% glycerol, 2% SDS, and 0.01% bromphenol blue) and loaded directly onto the gel. Pharmacia I34W Calibration Kit protein standards were used for MW markers, and the gels were silver stained. Under these conditions only a single band is visible with silver staining.

Fractions containing peptides with like mobilities were pooled and then assayed for total protein content and for activity in the protein C activation assay as described below.

E. Assays for Thrombomodulin Analogs.

1. Materials

Rabbit thrombomodulin, hirudin and human Protein C were supplied by American Diagnostics. Human thrombin is available from a variety of noncommercial and commercial sources. Bovine thrombin was purchased from Miles Labs, Dallas, Texas. D-valyl-L-leucyl-L-arginine-p-nitroanilide (S-2266) and D-Phe-Pip-Arg-p-nitroanilide (S-2238) were purchased from Kabi Diagnostics.

Bovine serum albumin (fraction V), citrated human plasma, and APTT reagent were purchased from Sigma Chemicals. Microtiter plates were supplied by Corning (#25861-96). All other reagents were of the highest grade available.

2. Methods and Results.

i. Protein C Activation Assay (Chromogenic)

This assay was performed by mixing 20 µl each of the following proteins in a microtiter plate: thrombomodulin sample (unknown or standard), thrombin (3 nM), and Protein C (1.5 µM). The assay diluent for each protein was 20 mM Tris-HCl, 0.1 M NaCl, 2.5 mM $CaCl_2$, 5 mg/ml BSA, pH 7.4. The wells were incubated for 2 hours at 37° C., after which Protein C activation was terminated by the addition of 20 µl of hirudin (0.16 unit/µl, 370 nM) in assay diluent and incubation for an additional 10 minutes.

The amount of activated Protein C formed was detected by adding 100 µl of 1.0 mM S-2266 (in assay diluent), and continuing to incubate the plate at 37° C. The absorbance at 405 nm in each well was read every 10 seconds for 30 minutes, using a Molecular Devices plate reader. The absorbance data was stored, and the change in absorbance per second (slope) in each well was calculated. The change in absorbance per second is proportional to pmole/ml of activated Protein C.

This ratio was determined empirically using varying concentrations of totally activated Protein C. Samples containing 100% activated Protein C were generated by mixing Protein C at 0 to 1.5 µM with 60 nM rabbit TM and 30 nM thrombin, incubating for 0 to 4 hours, adding hirudin and measuring S2266 activity as above. Conditions under which 100% of the Protein C was activated were defined as those in which the S2266 activity (A405/sec) reached a plateau.

A unit of activity is defined as 1 pmole of activated Protein C generated per ml/min under the reagent conditions defined above. Alternatively, activity values are reported in comparison to native detergent solubilized rabbit thrombomodulin. By using amino acid analysis to deduce protein mass, it has been determined that 1 nmole of TM analog 6h/227–462 (see Table 4) has activity equivalent to 1 nmole of rabbit thrombomodulin. Other TM analogs are more active in this assay than 6h/227–462. For example, one TM analog comprising the 6 EFG-like domains with a leucine substituted for the methionine at amino acid position 388 by in vitro mutagenesis (see Table 4) has a specific activity about 2.2 times that of 6h/227–462.

ii. Protein C Cofactor Activity After Exposure to Oxidants

Chloramine-T (N-Chloro-p-toluenesulfonamide sodium salt, Sigma) was used to specifically test the resistance of the mutant TM analog peptides to oxidation. Transfection culture supernatant (1 ml) containing a peptide encoded by a mutant TM gene sequence or pTMHY101 (wild-type, aa 227–462) desalted into 1.5 ml of 0.2% N-ethylmorpholine (NEM), pH 7.0, 0.008% Tween 80 on a NAP-10 column (LKB/Pharmacia) and then lyophilzed and resuspended in 100 ul of the above buffer. The sample was divided equally and either 5 ul of water (control) of 5 ul of 0.1 M chloramine-T (final conc.=9.1 nM) was added. The samples were incubated at room temperature for 20 minutes, then passed over the NAP-5 column to remove any oxidant. The desalting buffer used was protein C assay diluent. The mutant peptide retained all of its activity after being exposed to chloramine-T whereas the wild type peptide was substantially inactivated.

iii. Inhibition of the Activated Partial Thromboplastin Time (APTT).

The formation of a clot from citrated plasma is triggered by the addition of brain cephalin in ellagic acid ("APTT reagent"), and calcium ion. The time required for the clot to form is reproducible and increases proportionally with the addition of thrombomodulin. Reagents for the APTT are incubated at 37° C. before mixing, except for the citrated plasma, which is kept at 4° C.

The reaction was carried out as follows: 100 μl of Sigma Citrated Plasma was added to a plastic cuvette (Sarstedt #67.742), incubated at 37° C. for 1 min; 100 μl of Sigma APTT reagent was added and the mixture incubated for 2 min at 37° C.; 100 μl of test sample (or control buffer) and 100 μl 25 mM $CaCl_2$ were added and the cuvette was immediately placed in a Hewlett-Packard 8451A spectrophotometer equipped with a circulating water bath to keep the cuvette at 37° C. during reading. The absorbance due to light scattering at 320 nm was measured every 0.5 seconds, from 15 to 120 seconds, timed from the addition of $CaCl_2$. A plot of absorbance vs. time yields a sigmoidal curve, with the clotting time defined as the time at which the slope is the steepest, corresponding to the inflection point of the curve.

Ex vivo APTT assays were performed in the manner described above with the exception that citrated plasma from the animal used in the in vivo experiment was used in place of the citrated plasma obtained commercially.

iv. Inhibition of thrombin clotting time (TCT) and prothrombin reaction (PT).

Both the PT and TCT are determined using the Hewlett-Packard 8452 A diode-array spectrophotometer used for the APTT. For the PT reaction, 90 ul of either TM analog 6h/227–462 or PBS was added to 20 ul thromboplastin and 90 ul 25 mM $CaCl_2$ in a cuvette. The mixture was incubated for 1 minute at 37° C., then 100 ul of citrated plasma was added. After loading the cuvette into the spectrophotometer, the absorbance due to light scattering at 320 nm was measured every 0.5 seconds, from 15 to 120 seconds, timed from the addition of the plasma. A plot of absorbance vs. time yields a sigmoidal curve, with the clotting time defined as the time at which the slope is the steepest, corresponding to the inflection point of the curve. The TCT is evaluated in the same manner. The initial reaction mixture contains 100 ul citrated plasma, 25 ul of 100 mM $CaCl_2$ and 62.5 ul of either PBS or TM analog. After 1 minute, 12.5 ul of thombin is added. The clotting time is measured as described above.

v. Direct anticoagulant activity—Inhibition of thrombin catalyzed conversion of fibrinogen to fibrin.

Thrombin and varying amounts of TM analog 6h/227–462 were incubated for 2 minutes at 37° C. in microtitre plate wells. The total initial reaction volume was 50 ul PBS+7.5 mM $CaCl_2$ and 90 nM thrombin. After initial incubation, 100 ul of 3.75 mg/ml human fibrinogen was added per well, and the thrombin induced formation of fibrin was followed by measuring the change in absorbance at 405 nm in a Molecular Devices Vmax spectrophotometer (Molecular Devices, Menlo Park, CA). The end-point of the assay was the time at which 50% of the final absorbance was reached. Residual thrombin activity was determined by reference to a thrombin standard curve, which linearly relates the reciprocal of the thrombin concentration to the clotting time. When amounts of detergent solubilized native rabbit thrombomodulin and TM analog 6h/227–462 exhibiting equal activity as measured by protein C cofactor activity are compared in the direct anticoagulant activity assay, the TM analog exhibits a significantly reduced ability to inhibit thrombin-mediated conversion of fibrinogen to fibrin (approximately 1/10).

vi. Inhibition of platelet activation and aggregation.

The effects of TM analog 6h/227–462 on thrombin activation of platelets was tested by the methods of Esmon, et al., (1983) J. Biol. Chem. 258:12238–12242. When evaluated using this assay, TM analog 6h/227–462 did not significantly inhibit the thrombin-mediated activation and aggregation of platelets.

viii. Additional measures of TM antithrombotic activity.

1) TM analog's inhibition of activation of Factor V by thrombin is measured by the method described by Esmon et al., *J. Bio. chem.*, (1982), 257:7944–7947.

2) Inhibition of the TM analog thrombin complex by antithrombin III and heparin cofactor II is measured as described by Jakubowski et al., 1986.

3) TM analog's inhibition of the inactivation of protein S by thrombin is measured by the method described by Thompson & Salem, *J. Clin. Invest.*, (1986), 78(1):13–17.

4) Inhibition of thrombin-mediated activation of Factor XIII is measured by the method of Polgar, et al., (1987) *Thromb. Heamostas.* 58:140.

EXAMPLE 2. In Vivo Activity of a TM analog in a Rodent Model of Deep Venous Thrombosis.

The ability of a TM analog to abrogate the formation of a thrombus was evaluated in a modified stasis/endothelial injury-induced venous thrombosis model in the rat (see Maggi, A. et al., (1987) *Haemostasis* 17:329–335 or Pescador, R. et al., (1989) *Thrombosis Research* 53:197–201). The vena cava of an anaesthetized male Sprague Dawley rat (450 gr) was surgically isolated, then the animal was treated by bolus injection into the femoral artery with a thrombomodulin analog (6h/227–462 which contains the 6 EGF-like domains of native thrombomodulin), standard heparin or normal saline (0.1 ml/rat), as a control. The dose of heparin was 45 units/rat. The dose of thrombomodulin analog was 100, 10, 1, 0.1 or 0.01 μg/rat. Two minutes post-injection, the inferior vena cava was ligated at the left renal vein to induce stasis, and the vascular endothelium was injured by gently pinching with forceps. After 10 minutes, the vena cava was excised and examined for the presence of a thrombus, which if present was removed and weighed. In all cases the animals treated with heparin or thrombomodulin analog (6h/227–462 ) at 100, 10, or 1 μg/rat showed no evidence of thrombus formation whereas the saline treated animals and those receiving the lowest dose of thrombomodulin analog (0.01 μg) had thrombi with an average weight of 14.9 mg/thrombus. The rats treated with 0.1 μg of thrombomodulin analog showed a trace amount of thrombus which was not large enough to be removed and weighed.

The dose range used in this study was selected based on an in vitro APTT assay in which 1 μg/ml of thrombomodulin analog was insufficient to prolong the APTT but the addition of 10 μg/ml resulted in a significant prolongation. The results of APTT assays done on plasma samples taken from each of the treated rats show no prolongation in the TM analog treated and control rats (100 μg TM analog=45 sec, all other doses TM analog and the saline controls=30–35 sec). However, the APTT in the heparin treated rats was significantly prolonged (100 sec.).

This experimental system is a directly comparable model for deep venous thrombosis in humans, which is characterized by vascular injury and reduced blood flow. The results described above demonstrate that very low doses of a TM analog that are able to act as a cofactor for thrombin-mediated activation of protein C yet have a substantially reduced ability to inhibit thrombin-mediated conversion of fibrinogen to fibrin are effective at preventing thrombus formation. Moreover, the absence of prolongation in the APTT measured ex vivo indicates that this TM analog has no systemic effect on coagulation parameters and, therefore, would not promote unsafe bleeding side effects.

EXAMPLE 3. In Vivo Activity of a TM Analog in a Primate Model of Both Venous and Arterial Thrombosis The antithrombotic properties of the thrombomodulin analogs were evaluated in an arteriovenous shunt model in the baboon using a slight modification of the method of Cadroy, Y. et al., (1989) *Journal of Laboratory and Clinical Medicine* 113:436–448, as described in Hanson S. R. and Harker, L. A. (1987) *Thrombosis and Haemostasis* 58:801–805. This model was chosen because of the hemostatic similarity between the baboon and man and because the arteriovenous shunt serves as a model for both arterial-type and venous-type thrombi.

Figure 2:
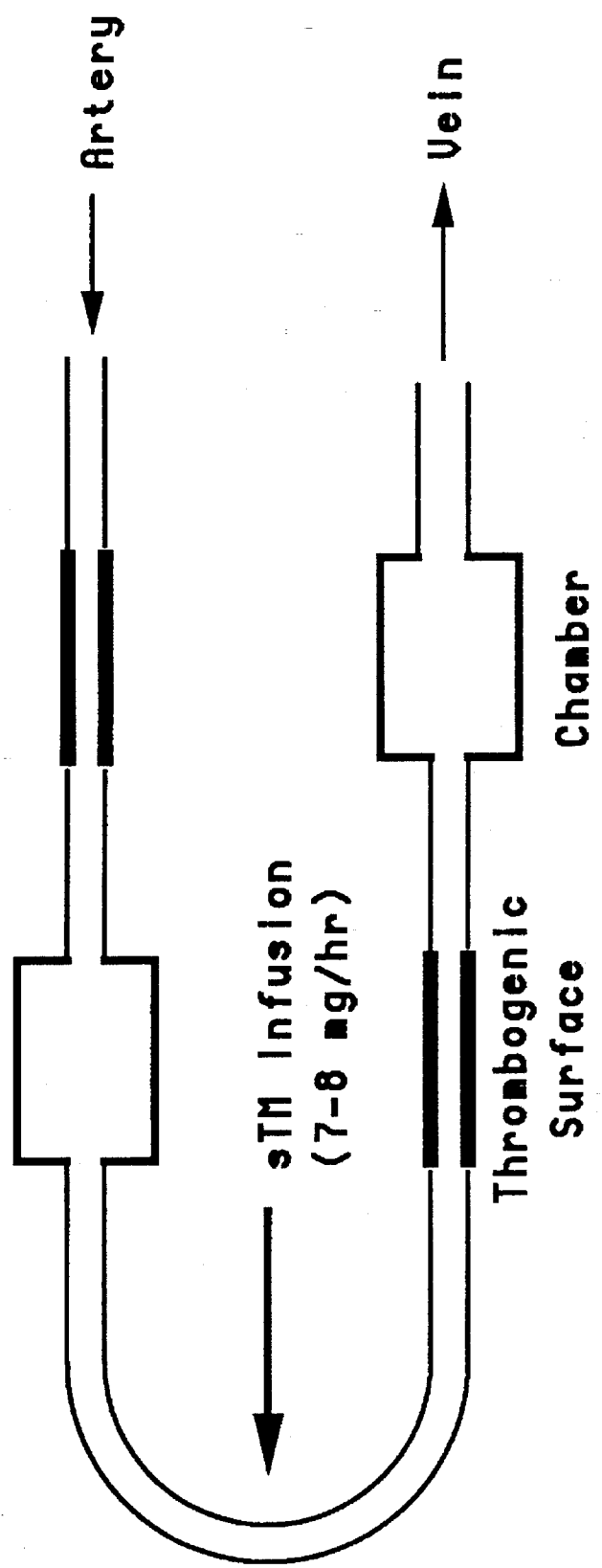
FIG. 2 is a diagram showing the arterio-venous shunt model in the baboon (See Example Three).

A silastic tubing shunt, modified with a piece of dacron tubing (3.2 mm in diameter) followed by a teflon chamber (9.3 mm in diameter), was inserted into the femoral artery of the baboon such that blood flowed out of the artery through the shunt and returned to the baboon via the femoral vein. (See FIG. 2). The dacron tubing presents a thrombogenic surface which stimulates the natural coagulation process, and in particular the deposition of platelets on the graft surface, and serves as a model for the generation of arterial, i.e. platelet rich, thrombi held together by fibrin. The chamber creates a stasis condition similar to that found in veins, where the rate of flow of the blood is reduced, and in particular mimics the area around venous valves, thus modeling flow conditions similar to those resulting in deep venous thrombosis. The thrombi formed in the chambers are venous-type, fibrin rich thrombi. Venous-type thrombi also contain platelets, but fewer than arterial-type thrombi. Thrombus formation in either the dacron graft or chamber is evaluated by measuring both platelet deposition and fibrin accretion. Platelet deposition is measured by removing platelets from the baboon, radiolabling the platelets with $^{111}$indium-oxine using the method of Cadroy,Y et al., (1989) *Journal of Clinical and Laboratory Medicine* 113(4):436–448, and then returning them to the animal. A scintillation camera, such as a Picker DC 4/11 Dyna scintillation camera (Picker Corp., Northford, Conn.), is positioned over the graft to directly measure the amount of radioactivity from the platelets being deposited as part of a thrombus as described in Cadroy, Y et al. As a second measure of thrombus formation, a 5 uCi dose of $^{125}$I-labeled baboon fibrinogen is given intravenously prior to insertion of the shunt. At the conclusion of the experiment, the shunt is removed, washed and and stored for 30 days to allow for the decay of $^{111}$indium radioactivity (half-life, 2.8 days). As $^{111}$indium decays much more rapidly than $^{125}$iodine, the detectable radioactivity remaining in the shunt represents the amount of fibrin deposited as part of a thrombus. Total fibrin deposition is calculated by dividing the counts per minute deposited by the amount of clottable fibrinogen present in the baboon blood as measured by the TCT assay. The first shunt in the series acts as a control for the second shunt.

Figure 3:
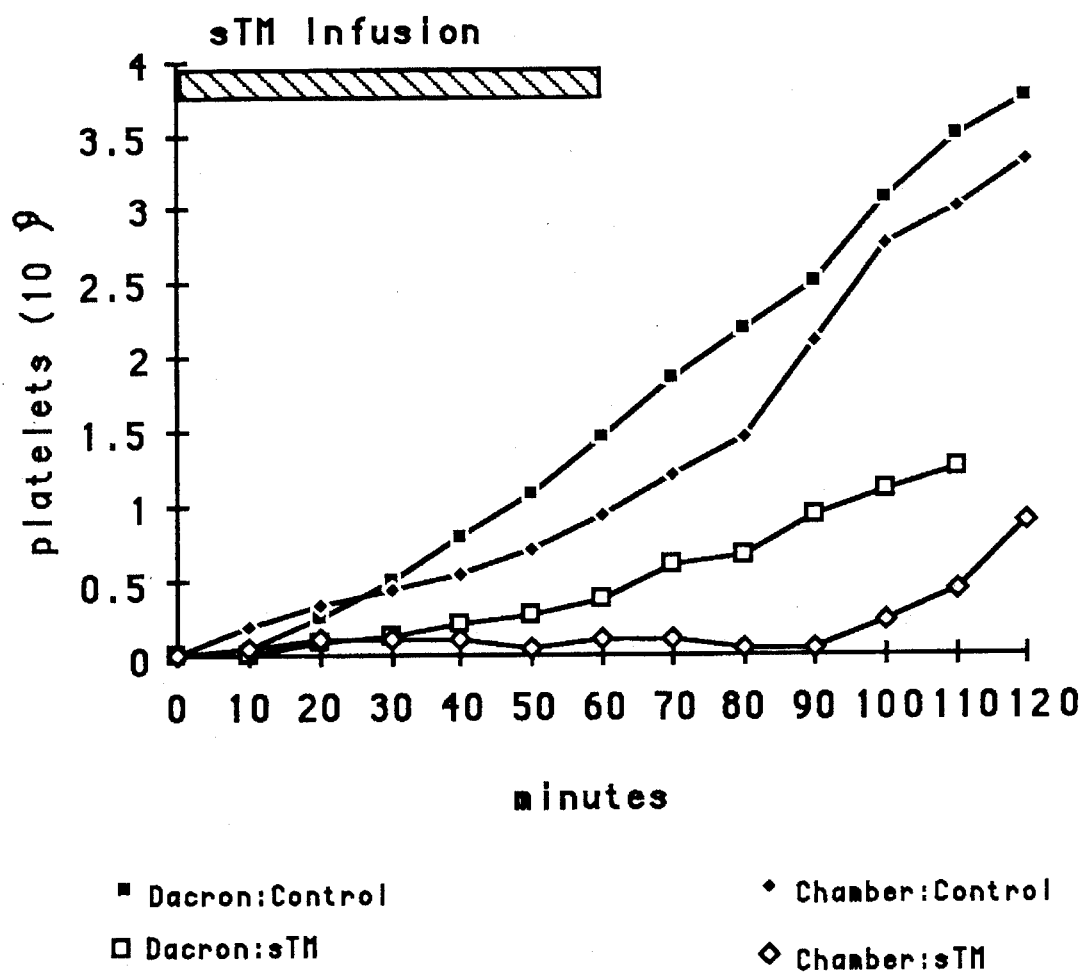
FIG. 3 shows platelet deposition in the arterio-venous shunt model with or without the thrombomodulin analog.

Two shunts in series were inserted into a baboon and the TM analog (6h/227–462 , see Table 4) infused at a point between the two shunts at a rate of 7 or 8 mg/hr for one hour. As can be seen in FIG. 3, platelets were deposited in both the chamber and the dacron graft in the control shunt, however, platelet deposition was significantly reduced following infusion of the TM analog into the second shunt.

These experiments demonstrate that a TM analog that has the ability to act as a cofactor for thrombin-mediated protein C activation and has a significantly reduce ability to inhibit thrombin-mediated conversion of fibrinogen to fibrin and thrombin-mediated activation and aggregation of platelets can prevent the formation of either arterial-type or venous-type thrombi in an in vivo model. Such a TM analog would therefore be useful for pharmaceutical treatment of any thrombotic disease, whether localized to the arteries or to the veins.

EXAMPLE 4. In Vivo Circulating Half-life

The circulating half-life of several TM analogs was evaluated using a modification of the protocol of Bakhit, C, et al., (1988) *Fibrinolysis* 2:31–36. Thrombomodulin analog was radiolabeled with $^{125}$iodine according to the lactoperoxidase method of Spencer, S. A., et al., (1988) *J. Biol. Chem.* 263:7862–7867. Approximately 100,000 cpm amount of labeled analog was injected into the femoral vein of an anesthetized mouse and XXX volume samples collected at selected time intervals. The level of radioactivity present in each sample, corresponding to the amount of radiolabeled thrombomodulin analog present in the circulation, was determined by counting in a gamma counter (Beckman) and the time necessary to decrease the amount of radioactivity in the circulation to one-half of its original value determined.

Three thrombomodulin analogs were evaluated using this method: 6h/227–462 (see above), 6h/227–462 that had been pretreated with hydrofluoric acid (HF) to remove some or all of the carbohydrate and 4t/227–462 (See Table 4 and Example 1.B.2). The treatment was done according to the method of Mort, A. J. and Lamport, T. A. (1977) *Analytical Biochemistry* 82:289–309. Briefly, 0.8 mg of TM analog (6h/227–462 ) was incubated in 1 ml anisole+10 mls HF (conc) at 0° C. for 1 hour under vacuum. After this time the volatile liquid was evaporated and the protein residue rinsed from the reaction chamber with two, 3 ml washes of 0.1 M acetic acid followed by two 3 ml washes of 50% acetic acid. The combined washes were extracted with 2 mls of ethylether to remove any residual anisole. The peptide containing aqueous phase was desalted on a PD10 column with 92% of the protein recovered from the starting material.

As can be seen from the results in Table 6, treating the TM analog so as to modify glycosylation can significantly alter its circulating half-life. This can be accomplished by either removing carbohydrate or altering its composition by expression in different cell types.

TABLE 1

| GGCACG GCGCAGCGGC AAGAAGTGTC TGGGCTGGGA CGGACAGGA | | | | | | | | | | | 46 |
|---|---|---|---|---|---|---|---|---|---|---|---|
| CGGACAGGAG AGGCTGTCGC CATCGGCGTC CTGTGCCCCT CTGCTCCGGC | | | | | | | | | | | 96 |
| ACGCCCTGT CGCAGTGCCC GCGCTTTCCC CGGCGCCTGC ACGCGGCGCG | | | | | | | | | | | 146 |
| CCTGGGTAAC | ATG | CTT | GGG | GTC | CTG | GTC | CTT | GGC | GCG | CTG | GCC | 189 |
|  | Met | Leu | Gly | Val | Leu | Val | Leu | Gly | Ala | Leu | Ala | |

TABLE 1-continued

| | | | | | | -15 | | | | -10 | | | |
|---|---|---|---|---|---|---|---|---|---|---|---|---|---|
| CTG Leu | GCC Ala | GGC Gly -5 | CTG Leu | GGG Gly | TTC Phe | CCC Pro -1 | GCA Ala +1 | CCC Pro | GCA Ala | GAG Glu | CCG Pro 5 | CAG Gln | CCG Pro | 231 |
| GGT Gly | GGC Gly | AGC Ser 10 | CAG Gln | TGC Cys | GTC Val | GAG Glu | CAC His 15 | GAC Asp | TGC Cys | TTC Phe | GCG Ala | CTC Leu 20 | TAC Tyr | 273 |
| CCG Pro | GGC Gly | CCC Pro | GCG Ala 25 | ACC Thr | TTC Phe | CTC Leu | AAT Asn | GCC Ala 30 | AGT Ser | CAG Gln | ATC Ile | TGC Cys | GAC Asp 35 | 315 |
| GGA Gly | CTG Leu | CGG Arg | GGC Gly | CAC His 40 | CTA Leu | ATG Met | ACA Thr | GTG Val | CGC Arg 45 | TCC Ser | TCG Ser | GTG Val | GCT Ala | 357 |
| GCC Ala 50 | GAT Asp | GTC Val | ATT Ile | TCC Ser | TTG Leu 55 | CTA Leu | CTG Leu | AAC Asn | GGC Gly | GAC Asp 60 | GGC Gly | GGC Gly | GTT Val | 399 |
| GGC Gly | CGC Arg 65 | CGG Arg | CGC Arg | CTC Leu | TGG Trp | ATC Ile 70 | GGC Gly | CTG Leu | CAG Gln | CTG Leu | CCA Pro 75 | CCC Pro | GGC Gly | 441 |
| TGC Cys | GGC Gly | GAC Asp 80 | CCC Pro | AAG Lys | CGC Arg | CTC Leu | GGG Gly 85 | CCC Pro | CTG Leu | CGC Arg | GGC Gly | TTC Phe 90 | CAG Gln | 483 |
| TGG Trp | GTT Val | ACG Thr | GGA Gly 95 | GAC Asp | AAC Asn | AAC Asn | ACC Thr | AGC Ser 100 | TAT Tyr | AGC Ser | AGG Arg | TGG Trp | GCA Ala 105 | 525 |
| CGG Arg | CTC Leu | GAC Asp | CTC Leu | AAT Asn 110 | GGG Gly | GCT Ala | CCC Pro | CTC Leu | TGC Cys 115 | GGC Gly | CCG Pro | TTG Leu | TGC Cys | 567 |
| GTC Val 120 | GCT Ala | GTC Val | TCC Ser | GCT Ala | GCT Ala 125 | GAG Glu | GCC Ala | ACT Thr | GTG Val | CCC Pro 130 | AGC Ser | GAG Glu | CCG Pro | 609 |
| ATC Ile | TGG Trp 135 | GAG Glu | GAG Glu | CAG Gln | CAG Gln | TGC Cys 140 | GAA Glu | GTG Val | AAG Lys | GCC Ala | GAT Asp 145 | GGC Gly | TTC Phe | 651 |
| CTC Leu | TGC Cys | GAG Glu 150 | TTC Phe | CAC His | TTC Phe | CCA Pro | GCC Ala 155 | ACC Thr | TGC Cys | AGG Arg | CCA Pro | CTG Leu 160 | GCT Ala | 693 |
| GTG Val | GAG Glu | CCC Pro | GGC Gly 165 | GCC Ala | GCG Ala | GCT Ala | GCC Ala | GCC Ala 170 | GTC Val | TCG Ser | ATC Ile | ACC Thr | TAC Tyr 175 | 735 |
| GGC Gly | ACC Thr | CCG Pro | TTC Phe | GCG Ala 180 | GCC Ala | CGC Arg | GGA Gly | GCG Ala | GAC Asp 185 | TTC Phe | CAG Gln | GCG Ala | CTG Leu | 777 |
| CCG Pro 190 | GTG Val | GGC Gly | AGC Ser | TCC Ser | GCC Ala 195 | GCG Ala | GTG Val | GCT Ala | CCC Pro | CTC Leu 200 | GGC Gly | TTA Leu | CAG Gln | 819 |
| CTA Leu | ATG Met 205 | TGC Cys | ACC Thr | GCG Ala | CCG Pro | CCC Pro 210 | GGA Gly | GCG Ala | GTC Val | CAG Gln | GGG Gly 215 | CAC His | TGG Trp | 861 |
| GCC Ala | AGG Arg | GAG Glu 220 | GCG Ala | CCG Pro | GGC Gly | GCT Ala | TGG Trp 225 | GAC Asp | TGC Cys | AGC Ser | GTG Val | GAG Glu 230 | AAC Asn | 903 |
| GGC Gly | GGC Gly | TGC Cys | GAG Glu 235 | CAC His | GCG Ala | TGC Cys | AAT Asn | GCG Ala 240 | ATC Ile | CCT Pro | GGG Gly | GCT Ala | CCC Pro 245 | 945 |
| CGC Arg | TGC Cys | CAG Gln | TGC Cys | CCA Pro 250 | GCC Ala | GGC Gly | GCC Ala | GCC Ala | CTG Leu 255 | CAG Gln | GCA Ala | GAC Asp | GGG Gly | 987 |
| CGC Arg 260 | TCC Ser | TGC Cys | ACC Thr | GCA Ala | TCC Ser 265 | GCG Ala | ACG Thr | CAG Gln | TCC Ser | TGC Cys 270 | AAC Asn | GAC Asp | CTC Leu | 1029 |
| TGC Cys | GAG Glu 275 | CAC His | TTC Phe | TGC Cys | GTT Val | CCC Pro 280 | AAC Asn | CCC Pro | GAC Asp | CAG Gln | CCG Pro 285 | GGC Gly | TCC Ser | 1071 |
| TAC Tyr | TCG Ser | TGC Cys 290 | ATG Met | TGC Cys | GAG Glu | ACC Thr | GGC Gly 295 | TAC Tyr | CGG Arg | CTG Leu | GCG Ala | GCC Ala 300 | GAC Asp | 1113 |
| CAA Gln | CAC His | CGG Arg | TGC Cys 305 | GAG Glu | GAC Asp | GTG Val | GAT Asp | GAC Asp 310 | TGC Cys | ATA Ile | CTG Leu | GAG Glu | CCC Pro 315 | 1155 |
| AGT Ser | CCG Pro | TGC Cys | CCG Pro | CAG Gln 320 | CGC Arg | TGT Cys | GAG Glu | GTC Val | AAC Asn | ACA Thr 325 | CAG Gln | GGT Gly | GGC Gly | 1197 |
| TTC Phe | GAG Glu | TGC Cys | CAC His | TGC Cys 330 | TAC Tyr | CCT Pro | AAC Asn | TAC Tyr | GAC Asp | CTG Leu | GTG Val 340 | GAC Asp | GGC Gly | 1239 |
| TGT Cys | GTG Val 345 | GAG Glu | CCC Pro | GTG Val | GAC Asp | CCG Pro 350 | TGC Cys | TTC Phe | AGA Arg | GCC Ala | AAC Asn 355 | TGC Cys | GAG Glu | 1281 |

TABLE 1-continued

| | | | | | | | | | | | | | | |
|---|---|---|---|---|---|---|---|---|---|---|---|---|---|---|
| TAC Tyr | CAG Gln | TGC Cys 360 | CAG Gln | CCC Pro | CTG Leu | AAC Asn | CAA Gln 365 | ACT Thr | AGC Ser | TAC Tyr | CTC Leu | TGC Cys 370 | GTC Val | 1323 |
| TGC Cys | GCC Ala | GAG Glu | GGC Gly 375 | TTC Phe | GCG Ala | CCC Pro | ATT Ile | CCC Pro 380 | CAC His | GAG Glu | CCG Pro | CAC His | AGG Arg 385 | 1365 |
| TGC Cys | CAG Gln | ATG Met | TTT Phe | TGC Cys 390 | AAC Asn | CAG Gln | ACT Thr | GCC Ala | TGT Cys 395 | CCA Pro | GCC Ala | GAC Asp | TGC Cys | 1405 |
| GAC Asp 400 | CCC Pro | AAC Asn | ACC Thr | CAG Gln | GCT Ala 405 | AGC Ser | TGT Cys | GAG Glu | TGC Cys | CCT Pro 410 | GAA Glu | GGC Gly | TAC Tyr | 1449 |
| ATC Ile | CTG Leu 415 | GAC Asp | GAC Asp | GGT Gly | TTC Phe | ATC Ile 420 | TGC Cys | ACG Thr | GAC Asp | ATC Ile | GAC Asp 425 | GAG Glu | TGC Cys | 1491 |
| GAA Glu | AAC Asn | GGC Gly 430 | GGC Gly | TTC Phe | TGC Cys | TCC Ser | GGG Gly 435 | GTG Val | TGC Cys | CAC His | AAC Asn | CTC Leu 440 | CCC Pro | 1533 |
| GGT Gly | ACC Thr | TTC Phe | GAG Glu 445 | TGC Cys | ATC Ile | TGC Cys | GGG Gly | CCC Pro 450 | GAC Asp | TCG Ser | GCC Ala | CTT Leu | GCC Ala 455 | 1575 |
| CGC Arg | CAC His | ATT Ile | GGC Gly | ACC Thr 460 | GAC Asp | TGT Cys | CCC Pro | GAC Asp | TCC Ser Gly 465 | GGC Lys | AAG Val | GTG Asp | GAC Gly | 1617 |
| GGT Gly 470 | GGC Asp | GAC Ser | AGC Gly | GGC Ser | TCT Gly 475 | GGC Glu | GAG Pro | CCC Pro | CCG Pro | CCC Ser 480 | AGC Pro | CCG Thr | ACG Pro | 1659 |
| GGC Gly | TCC Ser 485 | ACC Thr | TTG Leu | ACT Thr | CCT Pro | CCG Pro 490 | GCC Ala | GTG Val | GGG Gly | CTC Leu | GTG Val 495 | CAT His | TCG Ser | 1701 |
| GGC Gly | TTG Leu | CTC Leu 500 | ATA Ile | GGC Gly | ATC Ile | TCC Ser | ATC Ile 505 | GCG Ala | AGC Ser | CTG Leu | TGC Cys | CTG Leu 510 | GTG Val | 1743 |
| GTG Val | GCG Ala | CTT Leu | TTG Leu 515 | GCG Ala | CTC Leu | CTC Leu | TGC Cys | CAC His 520 | CTG Leu | CGC Arg | AAG Lys | AAG Lys | CAG Gln 525 | 1785 |
| GGC Gly | GCC Ala | GCC Ala | AGG Arg | GCC Ala 530 | AAG Lys | ATG Met | GAG Glu | TAC Tyr | AAG Lys 535 | TGC Cys | GCG Ala | GCC Ala | CCT Pro | 1827 |
| TCC Ser 540 | AAG Lys | GAG Glu | GTA Val | GTG Val | CTG Leu 545 | CAG Gln | CAC His | GTG Val | CGG Arg | ACC Thr 550 | GAG Glu | CGG Arg | ACG Thr | 1869 |
| CCG Pro | CAG Gln | AGA Arg | CTC Leu | TGA OP | GCGGCCTCCG TCCAGGAGCC | | | | | | | | | 1904 |

TABLE 2 t-PA Signal Sequence

| | | | | | | | | | | | | |
|---|---|---|---|---|---|---|---|---|---|---|---|---|
| ATG Met | GAT Asp | GCA Ala -30 | ATG Met | AAG Lys | AGA Arg | GGG Gly | CTC Leu -25 | TGC Cys | TGT Cys | GTG Val | CTG Leu | CTG Leu -20 | CTG Leu |
| TGT Cys | GGA Gly | GCA Ala -15 | GTC Val | TTC Phe | GTT Val | TCG Ser | CCC Pro | AGC Ser | CAG Glu -10 | ¦ INTRON A ¦ | GAA Glu | ATC Ile |
| CAT His | GCC Ala -5 | CGA Arg -1 | TTC Phe 1+1 | AGA Arg | AGA Arg | GGA Gly | GCC Ala | AGA Arg | TCC Ser | | | |

Hypodermin A Signal Sequence - pHY1

| | | | | | | | | | | | |
|---|---|---|---|---|---|---|---|---|---|---|---|
| COD #1198 | | GATCATG Met | CTC Leu | AAG Lys | TTT Phe | GTT Val -15 | ATT Ile | TTA Leu | TTG Leu | TGC Cys | AGT Ser -10 | ATT Ile |
| GCC Ala | TAT Tyr | GTT Val -5 | TTC Phe | GGT Gly | GCC Ala | GTC Val | GTA Val -1 | CCA Pro +1 | AGA Arg | TCT Ser | CCC Pro | CGG Arg |
| COD #1199 | | | | | | | | | | | | |

TABLE 3

```
COD #1292
5'ATCGGATCC    TGC   GAA   AAC   GGC   GGC   TCC      primer/coding sequence
 BamHI         Cys   Glu   Asn   Gly   Gly   Phe
aa 427
COD #1293
5'GTGGGATCC    TGC   TTC   AGA   GCC   AAC   TGC      primer/coding sequence
 BamHI         Cys   Phe   Arg   Ala   Asn   Cys
aa 350
COD #1294
5'CAGGGATCC    TGC   ACC   CAG   ACT   GCC   TGT      primer/coding sequence
 BamHI         Cys   Asn   Gln   Thr   Ala   Cys
aa 390
COD #1408
5'  (CTG   GTG   GAC   GGC   GAG   TGT')            coding sequence
     GAC   CAC   CTG   CCG   CTC   ACA    CACCGCCGGC GCCT primer sequence
     Leu   Val   Asp   Gly   Glu   Cys            NotI
     aa 339
COD #1409
5'  (CGC   CAC   ATT   GGC   ACC   GAC   TGT)      coding sequence
     GCG   GTG   TAA   CCG   TGG   CTG   ACA    TCTCGCCGGC GTAG primer sequence
     Arg   His   Ile   Gly   Thr   Asp   Cys           NotI
     aa 456
COD #1410
5'  (CAC   GAG   CCG   CAC   GGA   CGT)             coding sequence
     GTG   CTC   GGC   GTG   TCC   ACG    GTCTCGCCGG CGTT primer sequence
     His   Glu   Pro   His   Arg   C            NotI
aa 381
COD #1411
5'  (CGC   CAC   ATT   GGC   ACC   GAC   TGT   TGA)  coding sequence
     GCG   GTG   TAA   CCG   TGG   CTG   ACA   ACT   CGCCGGCGT primer sequence
Arg   His   Ile   Gly   Thr   Asp   Cys   STOP   NotI
aa 456
COD #1412
5'  (GAC   GAC   GGT   TTC   ATC   TGC)             coding sequence
     CTG   CTG   CCA   AAA   GGA   TAC    GCGCGGCCGG CTG primer sequence
     Asp   Asp   Gly   Phe   Ile   Cys            NotI
aa 416
COD #1433
5'  (CTG   GTG   GAC   GGC   GAG   TGT   TGA)       coding sequence
     GAC   CAC   CTG   CCG   CTC   ACA   ATC   CGCCGGCGCC T primer sequence
Leu   Val   Asp   Gly   Glu   Cys   STOP   NotI
aa 339
COD #1434
5'  (CAC   GAG   CCG   CAC   GGA   CGT   TGA)       coding sequence
     GTG   CTC   GGC   GTG   TCC   ACG   ATC   CGCCGGCGTT primer sequence
     His   Glu   Pro   His   Arg   Cys   STOP       NotI
aa 381
COD #1435
5'  (GAC   GAC   GGT   TTC   ATC   TGC   TGA)       coding sequence
     CTG   CTG   CCA   AAG   GAT   ACG   ATC   CGCCGGCGGCTG primer sequence
     Asp   Asp   Gly   Phe   Ile   Cys   STOP         NotI
aa 416
COD #1480
5'  (TGT   GAC   TCC   GGC   AAG   GTG   GAC   TGA)  coding sequence
     ACA   CTG   AGG   CCG   TTC   CAC   CTG   ACT   CTTAAGCT primer sequence
     Cys   Asp   Ser   Gly   Cys   Val   Asp   STOP    EcoRi
aa 462
COD #1479
5'  (GGC   ACC   GAC   TGT   GAC   TCC   TGA)       coding sequence
     CCG   TGG   CTG   ACA   CTG   AGG   ACT   CTTAAGCAG
     Gly   Thr   Asp   Cys   Asp   Ser   STOP     EcoRI
aa 459
COD #1478
               His   Trp   Ala   Arg   Glu   Ala   Pro
5'CCATGGC      CAC   TGG   GCC   AGC   GAG   GCG   CCG    primer/coding
  BalI         His   Trp   Ala   Arg   Glu   Ala   Pro    Sequence
    aa 216
COD #1481
5'  (CCG   GCC   GTG   GGG   CTC   GTG   CAT   TCG   TGA)  coding sequence
     GGC   CGG   CAC   CCC   GAG   CAC   GTA   AGC   ACT   CGCCGGCGGT A primer seq.
     Pro   Ala   Val   Gly   Leu   Val   His   Ser   STOP    NotI
aa 490
```

TABLE 4

| Vector | TM a.a. Region | Domain |
|---|---|---|
| *Expression in Insect Cells* | | |
| pTMHY101 | aa 221–462 | EGFs 1–6 |
| pTMHY102 | aa 216–468 | EGFs 1–6 |
| pTMHY103 | aa 216–464 | EGFs 1–6 |
| pTHR10 | aa 227–462 | EGFs 1–6 |
| pTHR11 | aa 227–462:227–462 | EGFs 1–6 + EGFs 1–6 |
| pTHR22 | aa 350–462 | EGFs 4,5&6 |
| pTHR78 | aa 227–497 | EGFs 1–6 + O-linked glycosylation domain |
| pTHR13 | aa 227–462 | EGFs 1–6 |
| *Expression in Mammalian Cells* | | |
| pTHR13 | aa 227–462 | EGFs 1–6 |
| pTHR19 | aa 350–462 | EGFs 4,5&6 |
| pTHR20 | aa 227–462:227–462 | EGFs 1–6 + EGFs 1–6 |
| pTHR21 | aa 227–497 | EGFs 1–6 + O-linked glycosylation domain |

TABLE 5

Primers for replacing the Methionine at aa 291

Native sequence
| Pro | Asp | Gln | Pro | Gly | Ser | Tyr | Ser | Cys | Met |
|---|---|---|---|---|---|---|---|---|---|
| CCCC | GAC | CAG | CCG | GGC | TCC | TAC | TCG | TGC | ATG |
| CCCC | GAC | CAG | CCG | GGC | TCC | TAC | AGC | TGC | CTG |
| | | | | | | | | | Leu |

Mutant Primer 1580
| | CAG | CCG | GGC | TCC | TAC | TCG | TGC | CAG |
|---|---|---|---|---|---|---|---|---|
| | | | | | | | | Gln |

Mutant Primer 1581
| CCCC | GAC | CAG | CCG | GGC | TCC | TAC | TCG | TGC | GCA |
|---|---|---|---|---|---|---|---|---|---|
| | | | | | | | | | Ala |

Mutant Primer 1582
| Cys | Glu | Thr | Gly | Tyr | Arg | Leu | Ala | Ala | |
|---|---|---|---|---|---|---|---|---|---|
| TGC | GAG | ACC | GGC | TAC | CGG | CTG | GCG | GCC | G |
| TGC | GAG | ACC | GGC | TAC | CGG | CTG | GCG | GCC | G |
| TGC | GAG | ACT | GGC | TAC | CGG | CTG | GCG | GCC | G |
| TGC | GAG | ACC | GGC | TAC | CGG | CTG | GCG | GCC | G |

Primers for replacing the Methionine at aa 388

Native sequence
| Pro | His | Glu | Pro | His | Arg | Cys | Gln | Met | |
|---|---|---|---|---|---|---|---|---|---|
| CCC | CAC | GAG | CCG | CAC | AGG | TGC | CAG | ATG | |
| CCC | CAC | GAG | CCG | CAC | AGG | TGC | CAG | CTG | |
| | | | | | | | | Leu | |

Mutant Primer 1573
| CCC | CAC | GAG | CCG | CAC | AGG | TGT | CAA | CAG | |
|---|---|---|---|---|---|---|---|---|---|
| | | | | | | | | Gln | |

Mutant Primer 1583
| CCC | CAC | GAG | CCG | CAC | AGG | TGC | CAG | GCC | |
|---|---|---|---|---|---|---|---|---|---|
| | | | | | | | | Ala | |

Mutant Primer 1584
| Phe | Cys | Asn | Gln | Thr | Ala | Cys | Pro | Ala | |
|---|---|---|---|---|---|---|---|---|---|
| TTT | TGC | AAC | CAG | ACT | GCC | TGT | CCA | GCC | G |
| TTT | TGC | AAC | CAG | ACT | GCC | TGT | CCA | GCC | G |
| TTT | TGC | AAC | CAG | ACT | GCC | TGT | CCA | GCC | G |
| TTT | TGC | AAC | CAG | ACT | GCC | TGT | CCA | GCC | G |

TABLE 6

| Sample | Half-life (min) |
|---|---|
| 6h/227–462 | 2.7 |
| HF treated 6h/227–462 | 7.3 |
| 4t/227–462 | 8.1 |

What is claimed is:

1. A method of treating a thrombotic disease or condition by administering a therapeutically effective dose of a purified thrombomodulin analog, wherein said analog comprises a polypeptide having an amino acid sequence corresponding to the six epidermal growth factor and the O-linked glycosylation domains of native thrombomodulin, and wherein the O-lined glycosylation domain is modified by:

a. modification of the amino acid sequence of the O-linked glycosylation domain or deletion of an amino acid residue forming a glycosylation site, b. removal of sulfate substituents on sugars in the O-linked glycosylation domain, or c. deletion of the O-linked glycosylation domain, whereby addition of glycosaminoglycan to serine or threonine residues in the Olinked glycosylation domain is attenuated, said analog having approximately native ability to potentiate thrombin-mediated activation of protein C and having a reduced ability to inactivate thrombin-mediated conversion of fibrinogen to fibrin, each ability as compared with native thrombomodulin.

2. A method of claim 1 wherein the thrombomodulin analog is soluble in aqueous solution.

3. A method of claim 2 wherein the thrombomodulin analog is modified in the sugar residues of the O-linked glycosylation domain.

4. A method of claim 3 where the O-linked glycosylation domain has no sugar residues.

5. A method of claim 3 where the O-linked glycosylation domain has been modified to remove glycosylation sites.

6. A method of claim 3 where the O-linked glycosylation domain comprises sugars with no sulfate substituents.

7. A method of claim 2 wherein the O-linked glycosylation domain has been deleted.

8. A method of claim 1 wherein the analog, when compared to native detergent-solubilized rabbit thrombomodulin on the basis of equal units of protein C activation, has 80% or less of the capacity of the native thrombomodulin to inactivate thrombin-mediated conversion of fibrinogen to fibrin.

9. A method of claim 1 wherein the analog, when compared to native detergent solubilized rabbit thrombomodulin on the basis of equal units of protein C activation, has 50% or less of the capacity of the native thrombomodulin to inactivate thrombin-mediated conversion of fibrinogen to fibrin.

10. A method of claim 1 wherein the analog is resistant to oxidation.

11. A method of claim 1 wherein the thrombomodulin analog does not comprise chondroitin sulfate.

12. A method of claim 1 wherein the thrombomodulin analog is modified at amino acid position 472, 474 or both, where said analog is numbered in accordance with native thrombomodulin and the modification is the deletion of the serine naturally occurring at the specified position.

13. A method of claim 12, wherein the serine residue at position 472 of said thrombomodulin analog is deleted.

14. A method of claim 12, wherein the serine residue at position 474 of said thrombomodulin analog is deleted.

15. A sterile composition useful for treating a thrombotic disease or condition in mammals, comprising a therapeutically effective dose of a purified thrombomodulin analog, wherein said analog comprises a polypeptide having an amino acid sequence corresponding to the six epidermal growth factor and the O-linked glycosylation domains of native thrombomodulin, and wherein the O-lined glycosylation domain is modified by:
   a. modification of the amino acid sequence of the O-linked glycosylation domain or deletion of an amino acid residue forming a glycosylation site,
   b. removal of sulfate substituents on sugars in the O-linked glycosylation domain, or
   c. deletion of the O-linked glycosylation domain, whereby addition of glycosaminoglycan to serine or threonine residues in the O-link glycosylation domain is attenuated, said analog having approximately native ability to potentiate thrombin-mediated activation of protein C and having a reduced ability to inactivate thrombin-mediated conversion of fibrinogen to fibrin, each ability as compared with native thrombomodulin.

16. A composition of claim 15 wherein the thrombomodulin analog, when compared to native detergent solubilized rabbit thrombomodulin on the basis of equal units of protein C activation, has 80% or less of the capacity of the native thrombomodulin to inactivate the thrombin-mediated conversion of fibrinogen to fibrin.

17. A composition of claim 15 wherein the thrombomodulin analog is modified in the O-linked glycosylation domain.

18. A composition of claim 17 where the O-linked glycosylation domain has no sugar residues.

19. A composition of claim 17 where the O-linked glycosylation domain has been modified to remove glycosylation sites.

20. A composition of claim 17 where the domain comprises sugars with no sulfate substituents.

21. A composition of claim 15 wherein the O-linked glycosylation domain has been deleted.

22. A composition of claim 15 wherein the analog is oxidation resistant.

23. A composition of claim 15 wherein the thrombomodulin analog does not comprise chondroitin sulfate.

24. A composition of claim 15 wherein the thrombomodulin analog is modified at amino acid position 472, 474 or both, where said analog is numbered in accordance with native thrombomodulin and the modification is the deletion of the serine naturally occurring at the specified position.

25. A method of claim 24, wherein the serine residue at position 472 of said thrombomodulin analog is deleted or replaced.

26. A method of claim 24, wherein the serine residue at position 474 of said thrombomodulin analog is deleted or replaced.

* * * * *